(12) United States Patent
Fang et al.

(10) Patent No.: US 8,768,472 B2
(45) Date of Patent: *Jul. 1, 2014

(54) MULTI-FREQUENCY NEURAL TREATMENTS AND ASSOCIATED SYSTEMS AND METHODS

(71) Applicant: Nevro Corporation, Menlo Park, CA (US)

(72) Inventors: Zi-Ping Fang, Beachwood, OH (US); Anthony V. Caparso, Alexandria, VA (US); Brian J. Erickson, Woodbury, MN (US); Konstantinos Alataris, Belmont, CA (US); Andre B. Walker, Monte Sereno, CA (US)

(73) Assignee: Nevro Corporation, Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/705,021

(22) Filed: Dec. 4, 2012

(65) Prior Publication Data

US 2013/0096643 A1    Apr. 18, 2013

Related U.S. Application Data

(63) Continuation of application No. 12/264,836, filed on Nov. 4, 2008.

(60) Provisional application No. 60/985,353, filed on Nov. 5, 2007.

(51) Int. Cl.
*A61N 1/00*    (2006.01)

(52) U.S. Cl.
USPC .......................................................... 607/46

(58) Field of Classification Search
USPC ............................................ 607/46, 2, 45, 43
See application file for complete search history.

(56) References Cited

U.S. PATENT DOCUMENTS

| | | | |
|---|---|---|---|
| 2,622,601 A | 12/1952 | Nemec | |
| 3,195,540 A | 7/1965 | Waller | |
| 3,817,254 A | 6/1974 | Maurer | |
| 3,822,708 A | 7/1974 | Zilber | |
| 3,893,463 A | 7/1975 | Williams | |

(Continued)

FOREIGN PATENT DOCUMENTS

| | | |
|---|---|---|
| EP | 1181947 | 2/2002 |
| GB | 2449546 A | 11/2008 |

(Continued)

OTHER PUBLICATIONS

U.S. Appl. No. 60/895,061, filed Mar. 15, 2007.*

(Continued)

*Primary Examiner* — Scott Getzow
(74) *Attorney, Agent, or Firm* — Perkins Coie LLP

(57) ABSTRACT

Multi-frequency neural treatments and associated systems and methods are disclosed. A method in accordance with a particular embodiment includes at least reducing patient pain by applying a first electrical signal to a first target location of the patient's spinal cord region at a frequency in a first frequency range of up to about 1,500 Hz, and applying a second electrical signal to a second target location of the patient's spinal cord region at a frequency in a second frequency range of from about 2,500 Hz to about 100,000 Hz.

12 Claims, 19 Drawing Sheets

(56) References Cited

U.S. PATENT DOCUMENTS

| | | |
|---|---|---|
| 4,014,347 A | 3/1977 | Halleck et al. |
| 4,023,574 A | 5/1977 | Nemec |
| 4,055,190 A | 10/1977 | Tany et al. |
| 4,155,366 A | 5/1979 | Di Mucci |
| 4,414,986 A | 11/1983 | Dickhudt et al. |
| 4,535,777 A | 8/1985 | Castel |
| 4,541,432 A | 9/1985 | Molina-Negro et al. |
| 4,550,733 A | 11/1985 | Liss et al. |
| 4,608,985 A | 9/1986 | Crish et al. |
| 4,649,935 A | 3/1987 | Charmillot et al. |
| 4,784,142 A | 11/1988 | Liss et al. |
| 4,841,973 A | 6/1989 | Stecker |
| RE33,420 E | 11/1990 | Sussman et al. |
| 4,989,605 A | 2/1991 | Rossen |
| 5,002,053 A | 3/1991 | Garcia-Rill |
| 5,335,657 A | 8/1994 | Terry, Jr. et al. |
| 5,514,175 A | 5/1996 | Kim et al. |
| 5,562,717 A | 10/1996 | Tippey et al. |
| 5,573,552 A | 11/1996 | Hansjurgens et al. |
| 5,643,330 A | 7/1997 | Holsheimer et al. |
| 5,716,377 A | 2/1998 | Rise |
| 5,776,170 A | 7/1998 | MacDonald et al. |
| 5,830,151 A | 11/1998 | Hadzic et al. |
| 5,853,373 A | 12/1998 | Griffith et al. |
| 5,893,883 A | 4/1999 | Torgerson et al. |
| 5,983,141 A | 11/1999 | Sluijter et al. |
| 5,995,872 A | 11/1999 | Bourgeois |
| 6,002,964 A | 12/1999 | Feler et al. |
| 6,014,588 A | 1/2000 | Fitz |
| 6,027,456 A | 2/2000 | Feler et al. |
| 6,161,044 A | 12/2000 | Silverstone |
| 6,167,305 A | 12/2000 | Cammilli et al. |
| 6,167,311 A | 12/2000 | Rezai |
| 6,176,242 B1 | 1/2001 | Rise |
| 6,233,488 B1 | 5/2001 | Hess |
| 6,238,423 B1 | 5/2001 | Bardy |
| 6,246,912 B1 | 6/2001 | Sluijter et al. |
| 6,341,236 B1 | 1/2002 | Osorio et al. |
| 6,356,786 B1 | 3/2002 | Rezai et al. |
| 6,405,079 B1 | 6/2002 | Ansarinia |
| 6,421,566 B1 | 7/2002 | Holsheimer |
| 6,440,090 B1 | 8/2002 | Schallhorn |
| 6,505,078 B1 | 1/2003 | King et al. |
| 6,510,347 B2 | 1/2003 | Borkan |
| 6,516,227 B1 | 2/2003 | Meadows et al. |
| 6,584,358 B2 | 6/2003 | Carter et al. |
| 6,609,030 B1 | 8/2003 | Rezai et al. |
| 6,622,048 B1 | 9/2003 | Mann et al. |
| 6,721,603 B2 | 4/2004 | Zabara et al. |
| 6,795,737 B2 | 9/2004 | Gielen et al. |
| 6,871,090 B1 * | 3/2005 | He et al. ............................ 607/2 |
| 6,885,888 B2 | 4/2005 | Rezai |
| 6,907,295 B2 | 6/2005 | Gross et al. |
| 6,923,784 B2 | 8/2005 | Stein |
| 6,928,230 B2 | 8/2005 | Squibbs |
| 6,928,320 B2 | 8/2005 | King |
| 6,950,707 B2 | 9/2005 | Whitehurst |
| 6,968,237 B2 | 11/2005 | Doan et al. |
| 6,990,376 B2 | 1/2006 | Tanagho et al. |
| 7,024,246 B2 | 4/2006 | Acosta et al. |
| 7,047,079 B2 | 5/2006 | Erickson |
| 7,082,333 B1 | 7/2006 | Bauhahn et al. |
| 7,117,034 B2 | 10/2006 | Kronberg |
| 7,146,224 B2 | 12/2006 | King |
| 7,149,574 B2 | 12/2006 | Yun et al. |
| 7,167,750 B2 | 1/2007 | Knudson et al. |
| 7,174,215 B2 | 2/2007 | Bradley |
| 7,180,760 B2 | 2/2007 | Varrichio et al. |
| 7,212,865 B2 | 5/2007 | Cory |
| 7,236,822 B2 | 6/2007 | Dobak, III |
| 7,239,912 B2 | 7/2007 | Dobak, III |
| 7,252,090 B2 | 8/2007 | Goetz |
| 7,260,436 B2 | 8/2007 | Kilgore et al. |
| 7,266,412 B2 | 9/2007 | Stypulkowski |
| 7,288,062 B2 | 10/2007 | Spiegel |
| 7,313,440 B2 | 12/2007 | Miesel |
| 7,324,852 B2 | 1/2008 | Barolat et al. |
| 7,326,181 B2 | 2/2008 | Katims |
| 7,333,857 B2 | 2/2008 | Campbell |
| 7,337,005 B2 | 2/2008 | Kim et al. |
| 7,346,398 B2 | 3/2008 | Gross et al. |
| 7,349,743 B2 | 3/2008 | Tadlock |
| 7,363,076 B2 | 4/2008 | Yun et al. |
| 7,389,145 B2 | 6/2008 | Kilgore et al. |
| 7,393,351 B2 | 7/2008 | Woloszko et al. |
| 7,493,172 B2 | 2/2009 | Whitehurst et al. |
| 7,502,652 B2 | 3/2009 | Gaunt et al. |
| 7,580,753 B2 | 8/2009 | Kim et al. |
| 7,599,737 B2 | 10/2009 | Yomtov et al. |
| 7,676,269 B2 | 3/2010 | Yun et al. |
| 7,689,289 B2 | 3/2010 | King |
| 7,734,340 B2 | 6/2010 | De Ridder |
| 7,742,810 B2 | 6/2010 | Moffitt et al. |
| 7,761,168 B2 | 7/2010 | Gross |
| 7,761,170 B2 | 7/2010 | Kaplan et al. |
| 7,778,704 B2 | 8/2010 | Rezai |
| 7,813,803 B2 | 10/2010 | Heruth et al. |
| 7,826,901 B2 | 11/2010 | Lee et al. |
| 7,860,570 B2 | 12/2010 | Whitehurst et al. |
| 7,877,136 B1 | 1/2011 | Moffitt et al. |
| 7,890,176 B2 | 2/2011 | Jaax et al. |
| 7,933,654 B2 | 4/2011 | Merfeld et al. |
| 7,937,145 B2 | 5/2011 | Dobak |
| 8,010,198 B2 | 8/2011 | Libbus et al. |
| 8,027,718 B2 | 9/2011 | Spinner et al. |
| 8,060,208 B2 | 11/2011 | Kilgore et al. |
| 8,082,039 B2 | 12/2011 | Kim et al. |
| 8,170,675 B2 | 5/2012 | Alataris et al. |
| 8,209,021 B2 | 6/2012 | Alataris et al. |
| 8,209,028 B2 | 6/2012 | Skelton et al. |
| 8,355,792 B2 | 1/2013 | Alataris et al. |
| 8,359,102 B2 | 1/2013 | Alataris et al. |
| 8,359,103 B2 | 1/2013 | Alataris et al. |
| 8,423,147 B2 | 4/2013 | Alataris et al. |
| 8,428,748 B2 | 4/2013 | Alataris et al. |
| 2002/0038137 A1 | 3/2002 | Stein |
| 2002/0055779 A1 | 5/2002 | Andrews |
| 2002/0128700 A1 | 9/2002 | Cross |
| 2003/0120323 A1 | 6/2003 | Meadows et al. |
| 2003/0220677 A1 | 11/2003 | Doan et al. |
| 2004/0015202 A1 | 1/2004 | Chandler et al. |
| 2004/0034394 A1 | 2/2004 | Woods et al. |
| 2004/0039425 A1 | 2/2004 | Greenwood-Van Meerveld |
| 2004/0073273 A1 | 4/2004 | Gluckman et al. |
| 2004/0093093 A1 | 5/2004 | Andrews |
| 2004/0162590 A1 | 8/2004 | Whitehurst et al. |
| 2004/0167584 A1 | 8/2004 | Carroll et al. |
| 2004/0193230 A1 | 9/2004 | Overstreet |
| 2004/0210270 A1 | 10/2004 | Erickson |
| 2005/0033381 A1 | 2/2005 | Carter et al. |
| 2005/0038489 A1 | 2/2005 | Grill |
| 2005/0060001 A1 | 3/2005 | Singhal et al. |
| 2005/0065575 A1 | 3/2005 | Dobak |
| 2005/0113882 A1 | 5/2005 | Cameron et al. |
| 2005/0119713 A1 | 6/2005 | Whitehurst et al. |
| 2005/0143789 A1 | 6/2005 | Whitehurst et al. |
| 2005/0153885 A1 | 7/2005 | Yun et al. |
| 2005/0245987 A1 | 11/2005 | Woods et al. |
| 2005/0246006 A1 | 11/2005 | Daniels |
| 2006/0004422 A1 | 1/2006 | De Ridder |
| 2006/0030895 A1 | 2/2006 | Simon et al. |
| 2006/0041285 A1 | 2/2006 | Johnson |
| 2006/0074456 A1 | 4/2006 | Pyles et al. |
| 2006/0095088 A1 | 5/2006 | De Ridder |
| 2006/0100671 A1 | 5/2006 | Ridder |
| 2006/0116742 A1 | 6/2006 | De Ridder |
| 2006/0161219 A1 | 7/2006 | Mock et al. |
| 2006/0161235 A1 | 7/2006 | King |
| 2006/0161236 A1 | 7/2006 | King |
| 2006/0190048 A1 | 8/2006 | Gerber |
| 2006/0229687 A1 | 10/2006 | Goetz et al. |
| 2006/0253182 A1 | 11/2006 | King |
| 2007/0021803 A1 | 1/2007 | Deem et al. |
| 2007/0032827 A1 | 2/2007 | Katims |

(56) References Cited

U.S. PATENT DOCUMENTS

| | | |
|---|---|---|
| 2007/0039625 A1 | 2/2007 | Heruth et al. |
| 2007/0049991 A1 | 3/2007 | Klostermann et al. |
| 2007/0060954 A1 | 3/2007 | Cameron et al. |
| 2007/0066997 A1 | 3/2007 | He et al. |
| 2007/0073353 A1 | 3/2007 | Rooney et al. |
| 2007/0073354 A1 | 3/2007 | Knudson et al. |
| 2007/0106337 A1 | 5/2007 | Errico et al. |
| 2007/0150034 A1 | 6/2007 | Rooney et al. |
| 2007/0156183 A1 | 7/2007 | Rhodes |
| 2007/0179559 A1 | 8/2007 | Giftakis et al. |
| 2007/0179579 A1 | 8/2007 | Feler et al. |
| 2007/0239226 A1 | 10/2007 | Overstreet |
| 2007/0244522 A1 | 10/2007 | Overstreet |
| 2007/0299482 A1 | 12/2007 | Littlewood et al. |
| 2008/0033511 A1 | 2/2008 | Dobak |
| 2008/0103570 A1 | 5/2008 | Gerber |
| 2008/0154333 A1 | 6/2008 | Knudson et al. |
| 2008/0167697 A1 | 7/2008 | Johnson |
| 2008/0183259 A1 | 7/2008 | Bly et al. |
| 2008/0234791 A1 | 9/2008 | Arle et al. |
| 2009/0036945 A1 | 2/2009 | Chancellor et al. |
| 2009/0054962 A1 | 2/2009 | Lefler et al. |
| 2009/0076561 A1 | 3/2009 | Libbus et al. |
| 2009/0132010 A1 | 5/2009 | Kronberg |
| 2009/0157141 A1 | 6/2009 | Chiao et al. |
| 2009/0157149 A1 | 6/2009 | Wahlgren et al. |
| 2009/0198306 A1 | 8/2009 | Goetz et al. |
| 2009/0204173 A1 | 8/2009 | Fang et al. |
| 2009/0204192 A1 | 8/2009 | Carlton et al. |
| 2009/0264973 A1 | 10/2009 | Boling et al. |
| 2009/0281595 A1 | 11/2009 | King et al. |
| 2009/0287274 A1 | 11/2009 | De Ridder |
| 2009/0319013 A1 | 12/2009 | Boling |
| 2009/0326611 A1 | 12/2009 | Gillbe |
| 2010/0016929 A1 | 1/2010 | Prochazka |
| 2010/0036454 A1 | 2/2010 | Bennett et al. |
| 2010/0069993 A1 | 3/2010 | Greenspan |
| 2010/0094375 A1 | 4/2010 | Donders et al. |
| 2010/0125313 A1 | 5/2010 | Lee |
| 2010/0137938 A1 | 6/2010 | Kishawi et al. |
| 2010/0191307 A1 | 7/2010 | Fang et al. |
| 2010/0241190 A1 | 9/2010 | Kilgore et al. |
| 2010/0249875 A1 | 9/2010 | Kishawi et al. |
| 2010/0274312 A1 | 10/2010 | Alataris et al. |
| 2010/0274314 A1 | 10/2010 | Alataris et al. |
| 2010/0274315 A1 | 10/2010 | Alataris et al. |
| 2010/0274316 A1 | 10/2010 | Alataris et al. |
| 2010/0274317 A1 | 10/2010 | Parker et al. |
| 2010/0274318 A1 | 10/2010 | Walker et al. |
| 2010/0274320 A1 | 10/2010 | Torgerson |
| 2010/0274326 A1 | 10/2010 | Chitre et al. |
| 2010/0324630 A1 | 12/2010 | Lee et al. |
| 2010/0331916 A1 | 12/2010 | Parramon et al. |
| 2011/0009919 A1 | 1/2011 | Carbunaru et al. |
| 2011/0009923 A1 | 1/2011 | Lee |
| 2011/0022114 A1 | 1/2011 | Navarro |
| 2011/0184486 A1 | 7/2011 | De Ridder |
| 2011/0184488 A1 | 7/2011 | De Ridder |
| 2011/0201977 A1 | 8/2011 | Tass |
| 2011/0276107 A1 | 11/2011 | Simon et al. |
| 2011/0282412 A1 | 11/2011 | Glukhovsky et al. |
| 2012/0016437 A1 | 1/2012 | Alataris et al. |
| 2012/0016438 A1 | 1/2012 | Alataris et al. |
| 2012/0016439 A1 | 1/2012 | Alataris et al. |
| 2012/0089200 A1 | 4/2012 | Ranu et al. |
| 2012/0158093 A1 | 6/2012 | Alataris et al. |
| 2012/0203304 A1 | 8/2012 | Alataris et al. |
| 2012/0209349 A1 | 8/2012 | Alataris et al. |
| 2012/0277833 A1 | 11/2012 | Gerber et al. |
| 2012/0283797 A1 | 11/2012 | De Ridder |
| 2013/0006325 A1 | 1/2013 | Woods et al. |
| 2013/0023951 A1 | 1/2013 | Greenspan |
| 2013/0041425 A1 | 2/2013 | Fang et al. |
| 2013/0066411 A1 | 3/2013 | Thacker et al. |
| 2013/0096644 A1 | 4/2013 | Fang et al. |
| 2013/0110196 A1 | 5/2013 | Alataris et al. |
| 2013/0123879 A1 | 5/2013 | Alataris et al. |
| 2013/0204173 A1 | 8/2013 | Kelly et al. |
| 2013/0204320 A1 | 8/2013 | Alataris et al. |
| 2013/0204321 A1 | 8/2013 | Alataris et al. |
| 2013/0204322 A1 | 8/2013 | Alataris et al. |
| 2013/0204323 A1 | 8/2013 | Thacker et al. |
| 2013/0204324 A1 | 8/2013 | Thacker |
| 2013/0204338 A1 | 8/2013 | Alataris et al. |
| 2013/0211487 A1 | 8/2013 | Fang et al. |
| 2013/0261695 A1 | 10/2013 | Thacker et al. |
| 2013/0261696 A1 | 10/2013 | Thacker et al. |
| 2013/0261697 A1 | 10/2013 | Parker |
| 2014/0031896 A1 | 1/2014 | Alataris et al. |

FOREIGN PATENT DOCUMENTS

| | | |
|---|---|---|
| JP | 2007528774 A | 10/2007 |
| WO | WO-02065896 A2 | 8/2002 |
| WO | WO-02092165 A1 | 11/2002 |
| WO | WO-2007082382 A1 | 7/2007 |
| WO | WO-2007117232 A1 | 10/2007 |
| WO | WO-2008039982 A2 | 4/2008 |
| WO | WO-2008045434 A2 | 4/2008 |
| WO | WO-2008106174 A1 | 9/2008 |
| WO | WO-2008121891 A1 | 10/2008 |
| WO | WO-2008153726 A2 | 12/2008 |
| WO | WO-2009018518 A1 | 2/2009 |
| WO | WO-2011014570 A1 | 2/2011 |

OTHER PUBLICATIONS

Wolter et al., "Continuous Versus Intermittent Spinal Cord Stimulation: An Analysis of Factors Influencing Clinical Efficacy," Neuromodulation: Technology at Neural Interface, www.neuromodulationjournal.com, 2011, 8 pages.

Alo et al., "New Trends in Neuromodulation for the Management of ; Neuropathic Pain," Neurosurgery, vol. 50, No. 4, Apr. 2002, 15 pages.

Van Butyen et al., "High Frequency Spinal Cord Stimulation for the ; Treatment of Chronic Back Pain Patients: Results of a Prospective ; Multicenter European Clinical Study," Neuromodulation Technology at the ; Neural Interface, International Neuromodulation Society, 2012, 8 pages.

U.S. Appl. No. 13/447,026, filed Apr. 13, 2012, Alataris et al.
U.S. Appl. No. 13/447,050, filed Apr. 13, 2012, Alataris et al.
U.S. Appl. No. 13/398,693, filed Feb. 16, 2012, Alataris et al.
U.S. Appl. No. 13/705,045, filed Dec. 4, 2012, Fang et al.
U.S. Appl. No. 13/620,235, filed Sep. 14, 2012, Alataris et al.
U.S. Appl. No. 13/725,770, filed Dec. 21, 2012, Alataris et al.
U.S. Appl. No. 13/728,965, filed Dec. 27, 2012, Alataris et al.

Barolat et al., "Multifactorial Analysis of Epidural Spinal Cord Stimulation," Sterotactic and Functional Neurosurgery, 1991; 56: 77-103.

Bhadra et al., "High Frequency electrical conduction block of the pudendal nerve," Journal of Neural Engineering—Institute of Physics Publishing, 2006, 8 pages.

Bhadra MD, Niloy et al., "High-Frequency Electrical Conduction Block of Mammalian Peripheral Motor Nerve," Muscle and Nerve, Dec. 2005, 9 pages.

Boger et al., "Bladder Voiding by Combined High Frequency Electrical Pudendal Nerve Block and Sacral Root Stimulation," Neurourology and Urodynamics, 27, 2008, 5 pages.

Bowman and McNeal, "Response of Single Alpha Motoneurons to High-Frequency Pulse Trains," Appl. Neurophysiol. 49, p121-138, 1986, 10 pages.

Burton, Charles, "Dorsal Column Stimulation: Optimization of Application," Surgical Neurology, vol. 4, No. 1, Jul. 1975, 10 pages.

Dapoigny, "Vagal influence on colonic motor activity in conscious nonhuman primates," American Journal Physiological Society, 1992, 6 pages.

DeRidder et al., "Are Paresthesias necessary for pain suppression in SCS—Burst Stimulation," BRAIN, Brain Research Center Antwerp of Innovative and Interdisciplinary Neuromodulation, 2010, 27 pages.

(56) References Cited

OTHER PUBLICATIONS

DeRidder et al., "Burst Spinal Cord Stimulation: Toward Paresthesia-Free Pain Suppression," www.neurosurgery-online.com, vol. 66, Nos. 5, May 2010, 5 pages.

Grill, Warren et al., "Stimulus Waveforms for Selective Neural Stimulation," IEEE Engineering in Medicine and Biology, Jul./Aug. 1995, pp. 375-385.

Holsheimer—Effectiveness of Spinal Cord Stimulation in the Management of Chronic Pain: Analysis of Techinical Drawbacks and Solutions, Neurosurgery, vol. 40, No. 5, May 1997, pp. 990-999.

Hopp et al., "Effect of anodal blockade of myelinated fibers on vagal c-fiber afferents," American Journal Physiological Society, Nov. 1980; 239(5), 9 pages.

Hoppenstein, Reuben, "Electrical Stimulation of the Ventral and Dorsal Columns of the Spianl Cord for Relief of Chronic Intractable Pain: Preliminary Report," Surgical Neurology, vol. 4, No. 1, Jul. 1975, 9 pages.

Huxely et al., "Excitation and Conduction in Nerve: Quantitative Analysis," "Science," Sep. 11, 1964; 145: 1154-9.

Jang et al., "Analysis of Failed Spinal Cord Stimulation Trails in the Treatment of Intractable Chronic Pain," J. Korean Neurosurg Soc 43, 2008, 5 pages.

Kilgore et al. "Nerve Conduction Block Utilizing High-Frequency Alternating Current" Medical & Biology Engineering and Computing, 2004, vol. 24, pp. 394-406.

Kumar et al., "Spinal Cord Stimulation in Treatment of Chronic Benign Pain: Challenges in Treatment Planning and Present Status, a 22-Year Experience," Neurosurgery, vol. 58, No. 3, Mar. 2006, 16 pages.

Linderoth et al., "Mechanisms of Spinal Cord Stimulation in Painful Syndromes: Role of Animal Models," Pain Medicine, vol. 7, No. S1, 2006, 13 pages.

Linderoth et al., "Physiology of Spinal Cord Stimulation: Review and Update," Neuromodulation, vol. 2, No. 3, 1999, 15 pages.

Mediati, R.D. "Mechanisms of Spinal Cord Stimulation," Florence, Oct. 2, 2002, 31 pages.

Melzack, Ronald et al., "Pain Mechanisms: A New Theory," Science, vol. 150, No. 3699, Nov. 19, 1965, 9 pages.

Muller and Hunsperger, "Helvetica Physiologica Acta—Reversible Blockierung der Erregungsleitung im Nerven durch Mittelfrequenz-Daverstrom," Schwabe & Co. Basel, vol. 25, Fasc. 1, 1967, 4 pages.

North et al., "Failed Back Surgery Syndrome: 5-year Follow-Up after Spinal Cord Stimulator Implantation," Neurosurgery, Offical Journal of the Congress of Neurological Surgeons, vol. 28, No. 5, May 1991, 9 pages.

North et al., "Spinal Cord Stimulation for Axial Low Back Pain," SPINE, vol. 30, No. 12, 2005, 7 pages.

North et al., "Spinal Cord Stimulation for Chronic, Intractable Pain: Experience over Two Decades," Neurosurgery, vol. 32, No. 2, Mar. 1993, 12 pages.

Oakley, John C., "Spinal Cord Stimulation Mechanisms of Action," SPINE vol. 27, No. 22, copyright 2002, 10 pages.

Paterson CA et al., "Determinants of Occurrence and Volume of Transpyloric Flow During Gastric Emptying of Liquids in Dogs: Importance of Vagal Input," Digital Disease and Science, vol. 45, No. 8, Aug. 2000,8 pages.

Shealy MD, C. Norman et al., "Electrical Inhibition of Pain by Stimulation of the Dorsal Columns: Preliminary Clinical Report," Anesthesia and Analgesia . . . Current Researches, vol. 446, No. 4, Jul.-Aug. 1967, 3 pages.

Simpson, BA, "Spinal Cord Stimulation in 60 cases of Intractable Pain." Journal of Neurology, Neurosurgery and Psychiatry, 1991; 54 pp. 196-199.

Simpson, BA, "Spinal Cord Stimulation." British Journal of Neurosurgery, Feb. 11, 1997 (1), 5-11, 7 pages.

Solomonow et al., "Control of Muscle Contractile Force through Indirect High-Frequency Stimulation," AM Journal of Physical Medicine, 1983, vol. 62, No. 3, pp. 71-82.

Tanner, J.A., "Reversible blocking of nerve conduction by alternating-current excitation," Nature, Aug. 18, 1962; 195: 712-3.

Urban et al., "Percutaneous epidural stimulation of the spinal cord for relief of pain—Long Term Results," Journal of Neurosurgery, vol. 48, Mar. 1978, 7 pages.

Van Den Honert et al. "Generation of Unidirectionally Propagated Action Potentials Nerve by Brief Stimuli" Science, vol. 26, pp. 1311-1312, (May 2010).

Van Den Honert, Mortimer JT, "A Technique for Collison Block of Peripheral Nerve: Frequency Dependence," MP-11 IEEE Trans. Biomed, Eng. 28: 379-382, 1981.

Woo MY, Campbell B. "Asynchronous Firing and Block of Peripheral Nerve Conduction by 20KC Alternating Current," Los Angeles Neuro Society, Jun. 1964; 87-94, 5 pages.

Zhang et al., "Simulation Analysis of Conduction Block in Myelinated Axons Induced by High-Frequency Biphasic Rectangular Pulses," IEEE Transactions on Biomedical Engineering, vol. 53., No. 7, Jul. 2006, 4 pages.

Bandra et al., Stimulation of High-Frequency Sinusoidal Electrical Block of Mammalian Myelinated Axons, J Comput Neurosco, 22:313-326, 2007.

Cuellar et al., "Effect of High Frequency Alternating Current ; on Spinal Afferent Nociceptive Transmission," Neuromodulation: Technology at the Neural Interface, 2012, 10 pages.

Kilgore et al. "Reversible Nerve Conduction Block Using Kilohertz Frequency Alternating Current," Neuromodulation Technology at the Neural Interface, International Neuromodulation Society, 2013, 13 pages.

Perruchoud et al., "Analgesic Efficacy of High-Frequency Spinal Cord Stimulation: A Randomized Double-Blind Placebo-Controlled Study," Neuromodulation: Technology at Neural Interface, International Neuromodulation Society, 2013, 7 pages.

Tiede et al., "Novel Spinal Cord Stimulation Parameters in Patients with Predominate Back Pain," Neuromodulation: Technology at the Neural Interface, 2013, 6 pages.

\* cited by examiner

MULTI-FREQUENCY NEURAL TREATMENTS AND ASSOCIATED SYSTEMS AND METHODS

CROSS-REFERENCE TO RELATED APPLICATION

The present application is a continuation application of U.S. patent application Ser. No. 12/264,836, filed Nov. 4, 2008, which claims priority to U.S. Provisional Application 60/985,353, filed Nov. 5, 2007 and incorporated herein by reference.

TECHNICAL FIELD

The present disclosure relates generally to methods and apparatuses for treating patient conditions, including chronic pain conditions via techniques that can include stimulating and blocking neuronal tissue associated with the spinal cord.

BACKGROUND

A. Neural Stimulation Treatments

Existing patient treatments include applying stimulation (e.g., up-regulating) signals to nerves, muscles or organs for treating a wide variety of medical disorders. Stimulation signal parameters (e.g., pulse width, frequency, and amplitude) are selected to initiate neural action potentials to be propagated along the nerve to an organ (e.g., brain or stomach).

Down-regulating signals also can be applied to nerve fibers. Certain signal parameters can result in a signal that inhibits the nerve or blocks the propagation of action potentials along the nerve. In general, the nerve conduction block is applied to nerves with down-regulating signals selected to block the entire cross-section or part of the cross section of the nerves (e.g., afferent, efferent, myelinated, and non-myelinated fibers) at the site where the down-regulating signal is applied.

In some systems, down-regulating signals are used to manage motor control over certain areas of a patient's body. For example, cryogenic nerve blocking of the vagus nerve to control motor activity is described in Dapoigny et al., "Vagal influence on colonic motor activity in conscious nonhuman primates," *Am. J. Physiol.*, 262: G231-G236 (1992). A cryogenic vagal block and the resulting effect on gastric emptying are described in Paterson C A, et al., "Determinants of Occurrence and Volume of Transpyloric Flow During Gastric Emptying of Liquids in Dogs: Importance of Vagal Input," *Dig Dis Sci*, (2000); 45:1509-1516.

B. Application to Chronic Pain

Applying up-regulating electrical energy to the spinal cord for the purpose of managing pain has been actively practiced since the 1960s. While a precise understanding of the interaction between the applied electrical energy and the nervous tissue is not fully appreciated, it is known that application of an electrical field to spinal nervous tissue can effectively mask certain types of pain transmitted from regions of the body associated with the stimulated tissue. Such spinal cord stimulation (SCS) for the treatment of chronic intractable pain was introduced by Shealy et al. (Anesth. Analg., 46, 489-491, 1967).

More specifically, applying up-regulating electrical pulses to the spinal cord associated with regions of the body (e.g., dermatomes) afflicted with chronic pain can induce paresthesia, or a subjective sensation of numbness or tingling, in the afflicted bodily regions. This paresthesia can effectively mask the non-acute pain sensations perceived at the brain.

Electrical energy, similar to that used to inhibit pain perception, also may be used to manage the symptoms of various motor disorders, for example, tremor, dystonia, spasticity, and the like. Motor spinal nervous tissue (e.g., nervous tissue from ventral nerve roots) transmits muscle/motor control signals. Sensory spinal nervous tissue (e.g., nervous tissue from dorsal nerve roots) transmits pain signals, as well as other sensory signals and proprioceptive signals.

Corresponding dorsal and ventral nerve roots depart the spinal cord "separately." Laterally from the spinal cord, the nervous tissue of the dorsal and ventral nerve roots are mixed, or intertwined. Accordingly, electrical stimulation intended to manage and control one condition (e.g., pain) can inadvertently interfere with nerve transmission pathways in adjacent nervous tissue (e.g., motor nerves).

Electrical energy is conventionally delivered through electrodes positioned on the dorsal column external to the dura layer surrounding a spinal cord. The electrodes are typically carried by a percutaneous lead, although a laminotomy lead also can be used. Percutaneous leads commonly have two or more electrodes and are positioned within an epidural space through the use of an insertion, or Touhy-like, needle. An example of an eight-electrode percutaneous lead is an OCTRODE® lead manufactured by Advanced Neuromodulation Systems, Inc. of Plano, Tex. Operationally, the insertion needle is passed through the skin, between the desired vertebrae, and into an epidural space located between a dural layer and the surrounding vertebrae. The stimulation lead is fed through the bore of the insertion needle and into the epidural space. Laminotomy leads generally have a wider, paddle-like shape, and are inserted via an incision rather than through a needle. For example, a small incision is made in the back of a patient to access the space between the dura and the surrounding vertebrae.

According to the "gate-control" theory of Melzak and Wall, (Science, 150,971-978, 1965), the suppression of pain sensations, accompanied by paresthesia, results from the activation of large cutaneous afferents ($A\alpha\beta$ fibers). Because these nerve fibers are part of the dorsal root (DR) fiber that ascends in the dorsal column (DC), paresthetic sensations can be evoked by both DC and DR stimulation.

The potential paresthesia coverage will strongly differ, however, depending on whether DC fibers or DR fibers are stimulated. When stimulating the DC fibers, the fibers corresponding to all dermatomes from the sacral ones up to the electrode level may be activated, thus resulting in broad paresthesia coverage. When stimulating DR fibers, however, the fibers will be activated in a limited number of rootlets close to the cathodal contact(s), thereby resulting in a paresthesia effect confined to one or two dermatomes at each body side.

There are several problems with existing Spinal Cord Stimulation (SCS) therapy techniques. One is the difficulty of obtaining a permanent optimal position of the lead(s), to cover the painful dermatomes with paresthesia. Another problem is the usually small range of stimulation amplitudes between the perception threshold (i.e., the threshold at which paresthesia is effected) and the discomfort threshold (i.e., the threshold at which the patient experiences pain or other discomfort), often preventing a complete coverage of the painful area by the paresthesia needed for maximum therapeutic effect (Holsheimer, Neurosurgery, 40, 5, 990-999, 1997).

SUMMARY

In some cases, low frequency signals are applied to the dorsal column to address chronic patient pain associated with a peripheral site. However, the dorsal roots also can be stimulated when low frequency stimulation is applied to the dorsal column to produce the paresthesia necessary to overcome the chronic pain. For example, the dorsal roots may be stimulated if the stimulation leads are placed too close to the dorsal root, and/or if the amplitude of the low frequency signal is increased to the discomfort threshold. The discomfort threshold at the dorsal root can be reached before the parethesia threshold (i.e., the threshold at which paresthesia is affected) is reached at the dorsal column. Hence, the clinician has limited freedom to increase the amplitude of the signal at the dorsal column to achieve the desired paresthesia effect, before discomfort is felt due to the dorsal root stimulation.

Aspects of the present disclosure are directed to managing chronic pain through the application of electrical energy to selected nervous tissue and, in particular embodiments, to methods and systems for treating chronic pain by applying neuromodulation therapies to one or more regions of neuronal tissue in the spinal region. As the term is used herein, the "spinal region" includes the nerves of the dorsal column, dorsal roots, and the dorsal roots ganglion, which are located within the dural layer.

A method for treating patient pain in accordance with a particular embodiment includes applying a first electrical signal to a first target location (e.g., a dorsal column) of the patient's spinal cord region at a frequency in a first frequency range of up to about 1,500 Hz. The method further includes applying a second electrical signal to a second target location (e.g., at least one of a dorsal root and a dorsal root ganglion) of the patient's spinal cord region at a frequency in a second frequency range of from about 2,500 Hz to about 100,000 Hz. In particular embodiments, the second frequency range can be from about 2,500 Hz to about 20,000 Hz, or about 3,000 Hz to about 10,000 Hz. Further embodiments include inducing paresthesia by applying the first electrical signal, and at least partially blocking patient discomfort resulting from applying the first electrical signal by applying the second electrical signal.

A method in accordance with another embodiment includes implanting a first electrode proximate to a dorsal column of the patient's spinal cord region, and implanting a second electrode proximate to at least one of a dorsal root and a dorsal root ganglion of the patient's spinal cord region. The method can further include applying a first electrical signal to the first electrode at a frequency in a first frequency range of up to about 1,500 Hz. If the patient experiences discomfort, a second electrical signal is applied to the second electrode at a frequency in a second frequency range of from about 2,500 Hz to about 100,000 Hz in combination with applying the first electrical signal, and without repositioning the first electrode. In particular embodiments, the second frequency range can be from about 2,500 Hz to about 20,000 Hz, or about 3,000 Hz to about 10,000 Hz.

Further embodiments are directed to systems for treating patient pain. In a particular embodiment, the system can include a controller having instructions for directing first electrical signals in a first frequency range of up to about 1,500 Hz, and directing second electrical signals in a second frequency range of from about 2,500 Hz to about 100,000 Hz. In particular embodiments, the second frequency range can be from about 2,500 Hz to about 20,000 Hz, or about 3,000 Hz to about 10,000 Hz. A first electrical signal delivery device can be electrically coupled to the controller to receive the first electrical signals, and can be configured to be positioned proximate to a first target location of the patient's spinal cord region (e.g., the dorsal column). A second electrical signal delivery device can be electrically coupled to the controller to receive the second electrical signals, and can be configured to be positioned proximate to a second target location of the patient's spinal cord region (e.g., at least one of a dorsal root and a dorsal root ganglion of the patient's spinal cord region).

DETAILED DESCRIPTION

Figure 1:
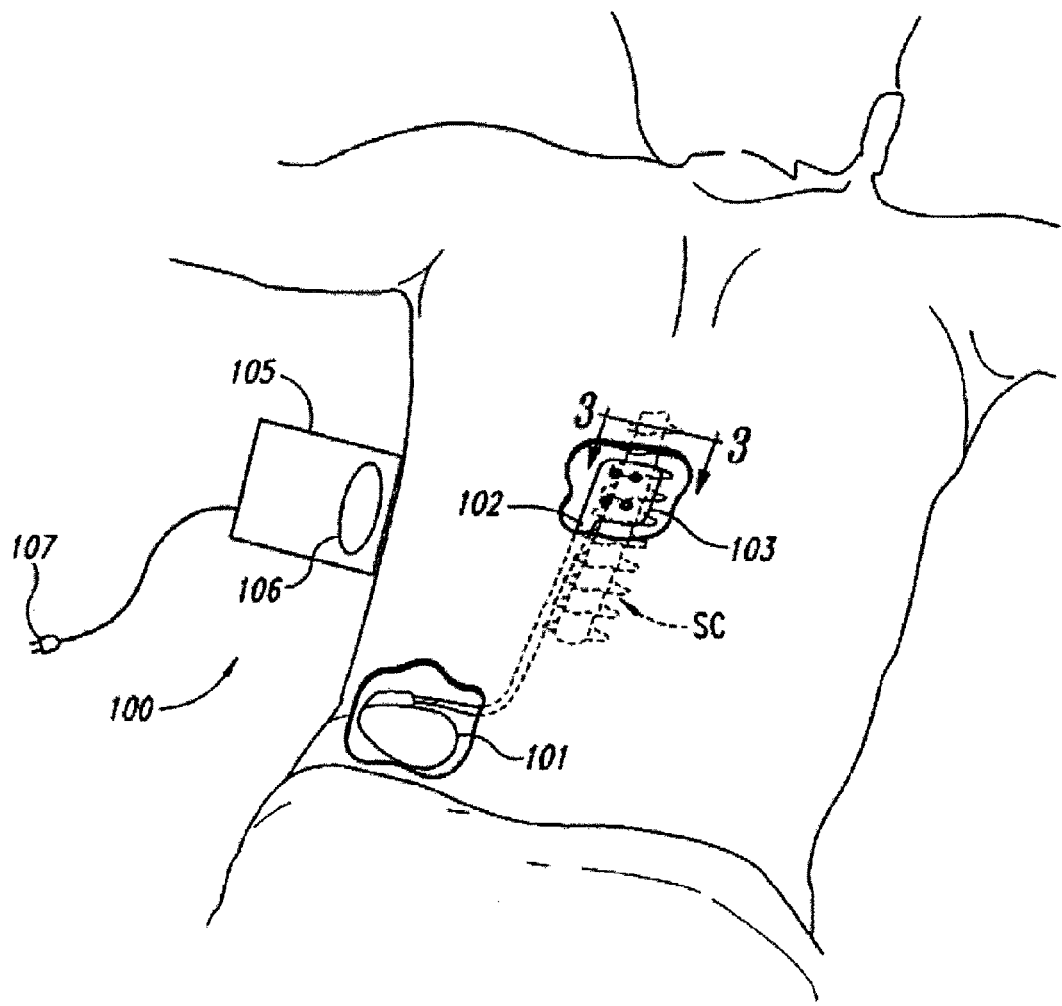
FIG. 1 is a schematic diagram of an implantable spinal stimulator with an electrode array applied to the spine in accordance with an embodiment of the present disclosure.

FIG. 1 schematically illustrates a representative therapy system 100 for providing relief from chronic pain, arranged relative to the general anatomy of a spinal cord SC of a patient. The therapy system 100 can include a controller (e.g., a pulse generator 101) implanted subcutaneously within the patient. The pulse generator 101 is attached via a lead body 102 to an electrode array 103 or other signal delivery device, which is implanted in close proximity to the spinal cord SC. The electrode array 103 can include multiple electrodes or electrode contacts carried by a support substrate. The pulse generator 101 or other controller transmits instructions and power to the electrode array 103 via the lead body 102 to apply therapy signals (e.g., electrical impulses) to the nerve fibers of the patient to up-regulate (e.g., stimulate) and/or down-regulate (e.g., block or partially block) the nerves. Accordingly, the pulse generator 101 can include a computer-readable medium containing the instructions. The pulse generator 101 and/or other elements of the system 100 can include one or more processors, memories and/or input/output devices. The pulse generator 101 can include multiple portions, e.g., for directing signals in accordance with multiple signal delivery parameters, housed in a single housing (as shown in FIG. 1) or in multiple housings.

In some embodiments, the pulse generator 101 can obtain power to generate the therapy signals from an external power source 105. The external power source 105, which is arranged external to the patient, can transmit power to the implanted pulse generator 101 using electromagnetic induction (e.g., RF signals). For example, the external power source 105 can include an external coil 106 that communicates with a corresponding coil (not shown) within the implantable pulse generator 101. The external power source 105 can be portable for ease of use.

In another embodiment, the pulse generator 101 can obtain the power to generate therapy signals from an internal power source. For example, the implanted pulse generator 101 can include a non-rechargeable battery or a rechargeable battery to provide the power. When the internal power source includes a rechargeable battery, the external power source 105 can be used to recharge the battery. The external power source 105 in turn can be recharged from a suitable power source e.g., via a standard power plug 107.

In still further embodiments, an external programmer (not shown) can communicate with the implantable pulse generator 101 via electromagnetic induction. Accordingly, a practitioner can update the therapy instructions provided by the pulse generator 101. Optionally, the patient may also have control over at least some therapy functions, e.g., starting and/or stopping the pulse generator 101.

Figure 2:
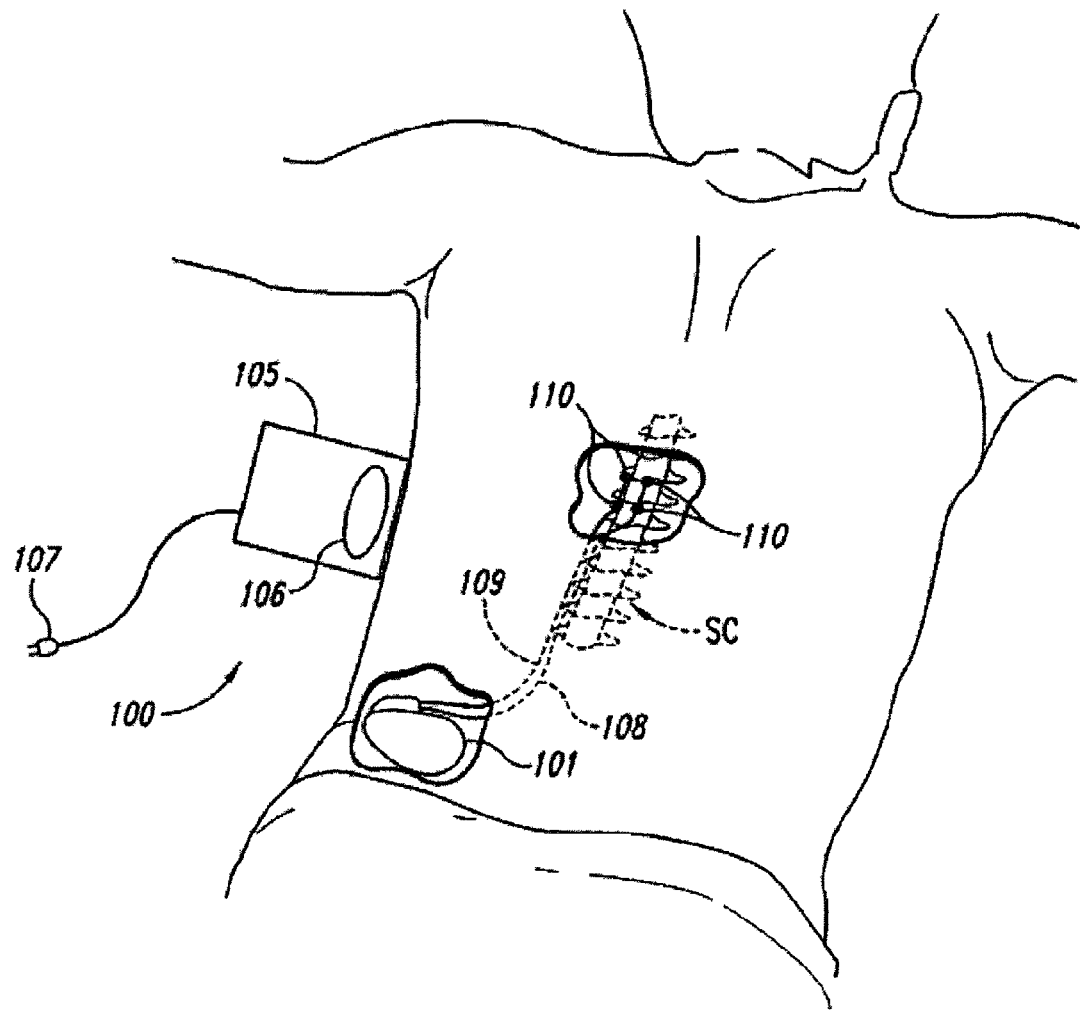
FIG. 2 is a schematic diagram of an implantable spinal stimulator with percutaneous leads and electrodes applied to the spine in accordance with another embodiment of the present disclosure.

FIG. 2 illustrates another therapy system 200 in which the implantable pulse generator 101 is connected to percutaneous lead bodies 108 and 109, which are in turn connected to electrodes 110. The leads 108, 109 and electrodes 110 are shown in a bipolar configuration with two electrodes 110 carried by each lead 108, 109. In other embodiments, however, the leads 108, 109 can each contain more electrodes 110 (e.g., three, four, five, eight, or more) for applying therapy signals. In any of the foregoing embodiments, the electrodes (e.g., the electrode array 103 or the electrodes 110 of the percutaneous leads 108,109) can be arranged adjacent different nerve fibers within the patient to enable the application of different types of therapy, as is discussed further below.

Figure 3:
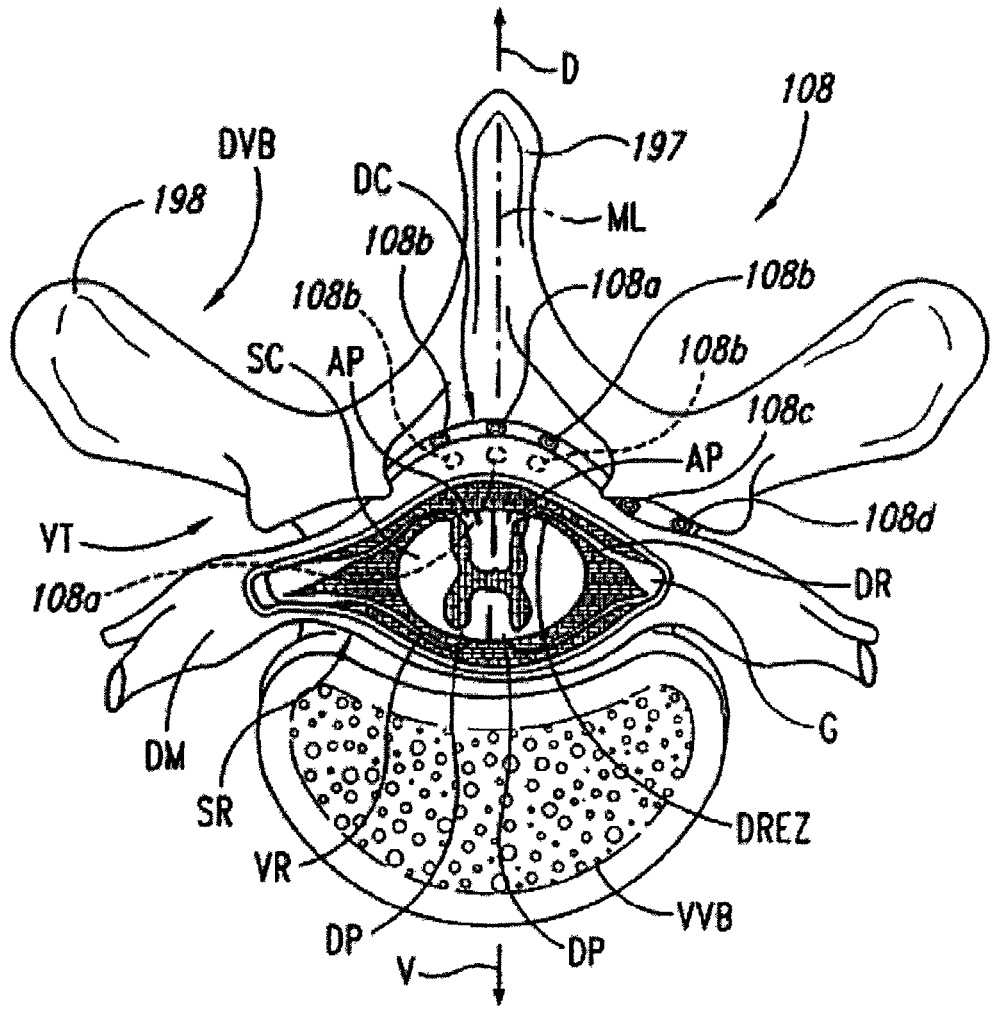
FIG. 3 is a partially schematic cross-sectional view of a spinal column taken along line 3-3 of FIG. 1 in accordance with an embodiment of the present disclosure.

FIG. 3 is a cross-sectional illustration of a spinal region SR that includes the spinal cord SC and an adjacent vertebra VT (based generally on information from Crossman and Neary, "Neuroanatomy," 1995 (publ. by Churchill Livingstone)), along with selected representative locations for representative leads 108 (shown as leads 108a-108d) in accordance with several embodiments of the disclosure. The spinal cord SC is situated between a ventrally located vertebral body VVB and a dorsally located vertebral body DVB that includes a transverse process 198 and spinous process 197. Arrows V and D identify ventral and dorsal directions, respectively. In particular embodiments, the vertebra VT and leads can be at T10 or T11 (e.g., for axial low back pain or leg pain) and in other embodiments, the leads can be placed at other locations. The spinal cord SC itself is located within the dura mater DM, which also surrounds portions of the nerves exiting the spinal cord SC, including the dorsal roots DR, dorsal root ganglia G and ventral roots VR. The spinal cord SC is illustrated as having identifiable areas of afferent and efferent fibers including ascending pathway areas AP and descending pathway areas DP.

The leads are generally positioned to stimulate tactile fibers and to avoid stimulating fibers associated with nociceptive pain transmission. In a particular embodiment, a lead 108a (e.g., a first lead) can be positioned centrally in a lateral direction (e.g., aligned with the spinal cord midline ML) to provide signals directly to the dorsal column DC of spinal cord SC. In other embodiments, the first lead can be located laterally from the midline ML. For example, single or paired leads can be positioned just off the spinal cord midline ML (as indicated by leads 108b) to provide signals to the dorsal column DC. One or more other leads (e.g., second leads) can be positioned proximate to the dorsal root DR or dorsal root entry zone DREZ (e.g., 1-4 mm from the spinal cord midline ML, as indicated generally by lead 108c), and/or proximate to the dorsal root ganglion G (as indicated by lead 108d). Other suitable locations for the second lead include the "gutter," also located laterally from the midline ML. In still further embodiments, the leads 108 may have other locations proximate to the spinal cord SC and/or proximate to other target neural populations e.g., laterally from the midline ML and medially from the dorsal root ganglion 194. For example, the leads can be located subdurally rather epidurally, as shown in dashed lines for midline lead 108a and off-midline leads 108b. The practitioner may select any of a variety of combinations of the foregoing locations, depending on the particular patient's needs and condition. In at least some embodiments, the practitioner can place two leads, each positioned to direct signals to a different target location (e.g., neural population) of the patient's spinal cord SC. In other embodiments, a single lead may have electrodes positioned at two or more target locations. In either case, individual electrodes can deliver signals with different characteristics to different neural populations to achieve a beneficial effect for the patient.

A. Therapy Options

In general, different types of therapy signals can be applied to the nerve fibers of a patient to different effect. For example, applying a low-frequency (LF) therapy signal to the nerve fibers of a patient can stimulate the nerve fibers to create an effect known in the art as "paresthesia," which creates a sensation of numbness in the patient. This paresthesia effect can mask chronic pain, providing relief to the patient. Such an application of therapy signals is generally known as Spinal Cord Stimulation (SCS) therapy. In a particular embodiment of the present disclosure, the LF signal can have a frequency in the range of up to about 1,500 Hz, and a pulse width equal to or less than half of the period of the signal. In a particular embodiment, the LF signal can have a frequency in the range of from about 40 Hz to about 500 Hz.

Applying a high-frequency (HF) therapy signal to the nerves can produce a block or partial block on the nerves. Accordingly, as used herein, the term "block" refers generally to an at least partial block (e.g., a partial or complete block), and the term "blocking signal" refers generally to a signal that creates an at least partial block. In addition, while it is believed that the block inhibits or prevents the transmission of neural signals, a desired effect on the patient (e.g., pain reduction) is not necessarily limited to such a mechanism, and in at least some embodiments, pain reduction may be achieved by one or more other mechanisms. This block inhibits and/or prevents excitatory responses from reaching the brain of the patient. Typically, the HF therapy signal includes a biphasic signal. In a particular embodiment, the HF therapy signal is a biphasic (alternating current) signal having a 50% duty cycle and a frequency in the range of from about 2,500 Hz to about 100,000 Hz. In particular embodiments, the HF signal can have a frequency in the range of from about 2,500 Hz to about 20,000 Hz, and in further particular embodiments, about 3,000 Hz to about 10,000 Hz.

Figure 4:
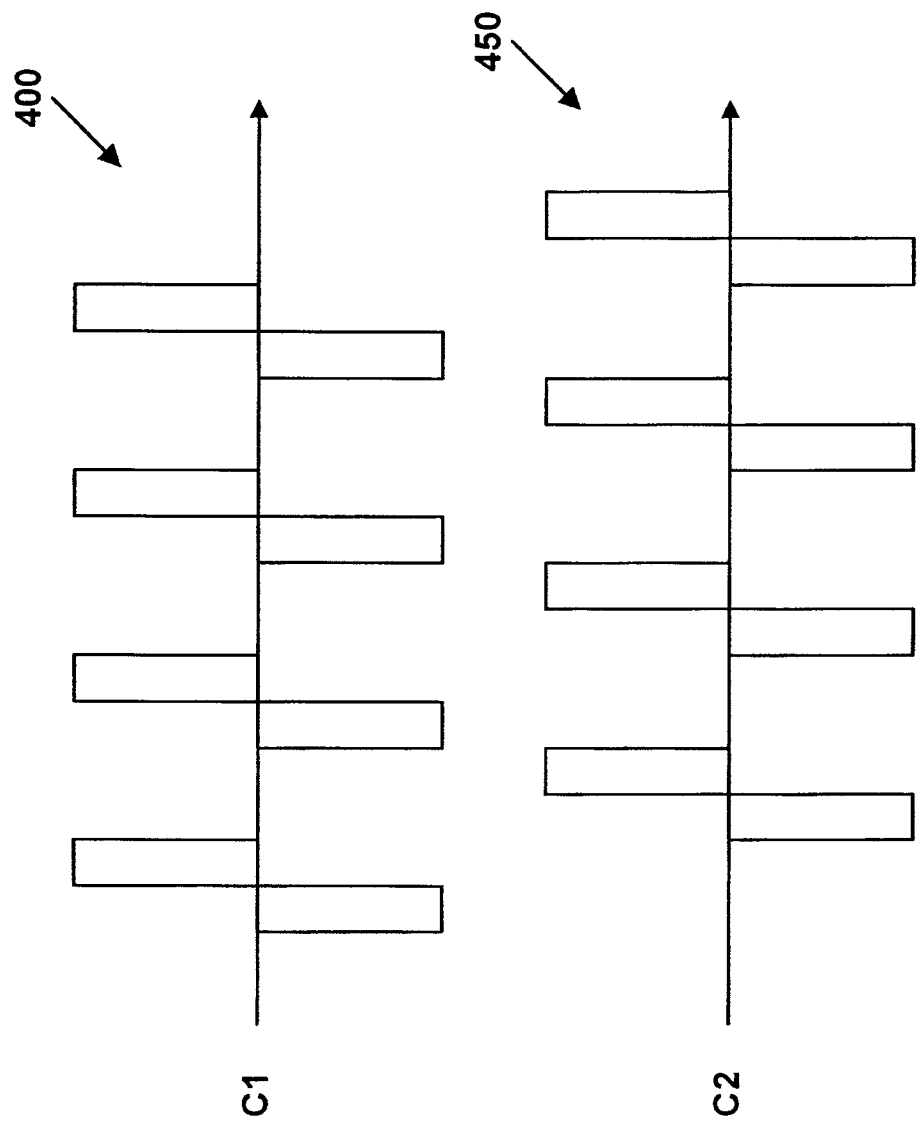
FIG. 4 illustrates examples of biphasic, charge balanced, square wave pulses applied to electrodes on different channels of a therapy system in accordance with an embodiment of the present disclosure.
Figure 5:
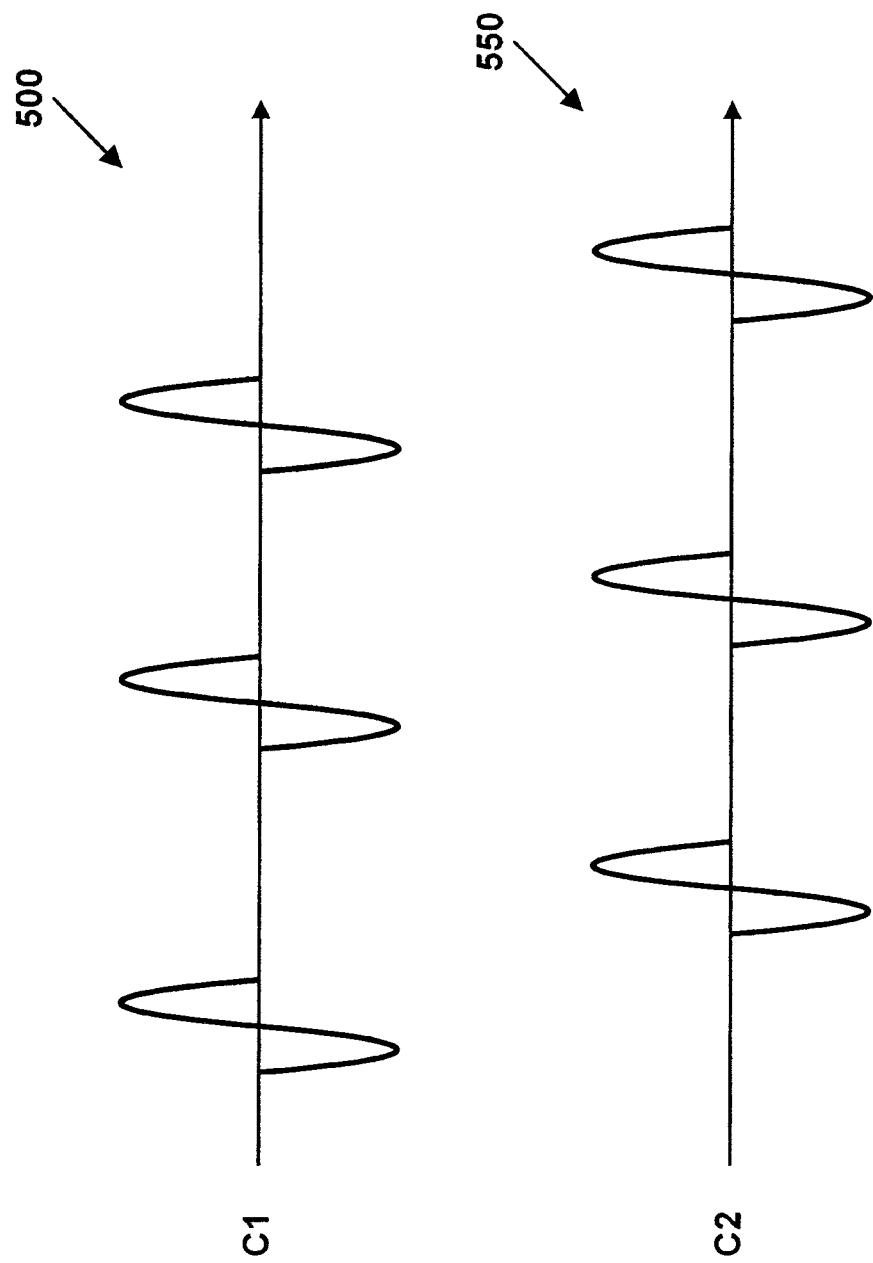
FIG. 5 illustrates examples of biphasic, charge balanced, sinusoidal wave pulses applied to electrodes on different channels of a therapy system in accordance with an embodiment of the present disclosure.

Representative examples of HF signal waveforms that can be applied to the dorsal column DC (FIG. 3) are shown in FIGS. 4 and 5. The signal waveforms shown in FIG. 4 include biphasic, charge balanced, square wave pulses. In the example shown, a first waveform 400 is applied to a first signal channel C1 and a second waveform 450 is applied to a second signal channel C2. In a particular embodiment, the waveform on the first signal channel C1 is interlaced with the waveform on the second signal channel C2 to minimize interaction between the signals 400, 450. This option is generally available when the HF signal is applied at a duty cycle of less than 50%, using one or more contacts that are shared between the first channel C1 and the second channel C2. When the HF signal has a 50% duty cycle, separate dedicated contacts can be used for each of the first and second channels C1, C2 to avoid interference between signals on the two channels. In still further embodiments, signal waveforms other than those shown in FIG. 4 can be used. For example, FIG. 5 illustrates biphasic, charge balanced, sinusoidal pulses 500, 550 which can be applied via the first and second signal channels C1, C2, respectively.

Detailed treatment processes for administering therapy signals for chronic pain management are described below. In certain embodiments, a physician or other practitioner can choose to combine two or more of the treatment processes described below for administering therapy for chronic pain management. The combination of the different types of therapy can provide pain relief on multiple fronts, providing extended coverage to the patient. For example, in one embodiment, multiple treatment processes can be applied to a patient simultaneously. In other embodiments, the therapies can be combined, but chronologically spaced, or offset, which can also have advantages. For example, as noted in further detail later, one therapy signal can be used to facilitate the initialization and/or the maintenance of another therapy signal.

1. Blocking at the Dorsal Column

Figure 6:
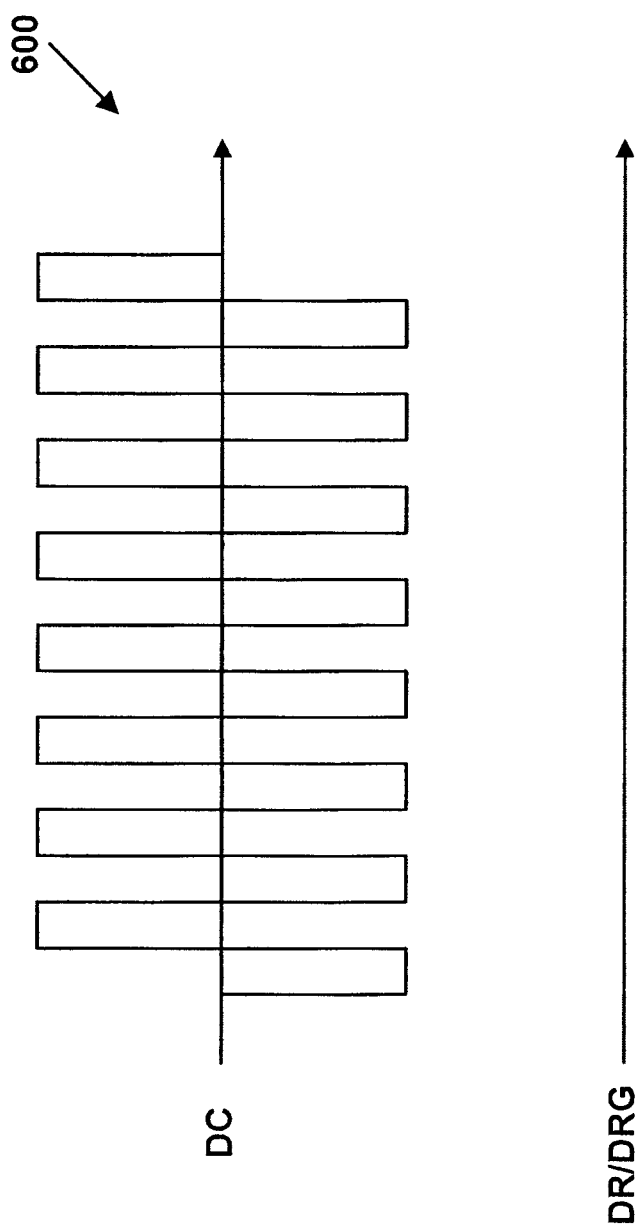
FIG. 6 is a schematic depiction of an example blocking signal applied to the dorsal column in accordance with an embodiment of the present disclosure.

A representative first treatment process for administering therapy for chronic pain management includes applying an HF blocking signal directly to the dorsal column DC of the patient. For example, FIG. 6 is a schematic depiction of a representative HF blocking signal 600 applied to the dorsal column DC. This HF blocking signal can be applied to the dorsal column DC in place of an LF stimulation signal to replace the pain relief provided by the paresthesia.

In general, the HF stimulation blocking signal 600 is applied to the dorsal column DC to establish a partial or total neuronal block at the dorsal column DC sufficient to block the chronic pain felt by the patient. The HF therapy signal can be applied to one or more select regions (e.g., vertebral levels) of the dorsal column DC to block transmission of pain signals from lower dermatomes. The HF blocking signal can inhibit or prevent the sensation of pain (e.g., to effect anesthesia) in the dermatomes corresponding to the selected regions.

2. Blocking at the Dorsal Root and/or the Dorsal Root Ganglion

Figure 7:
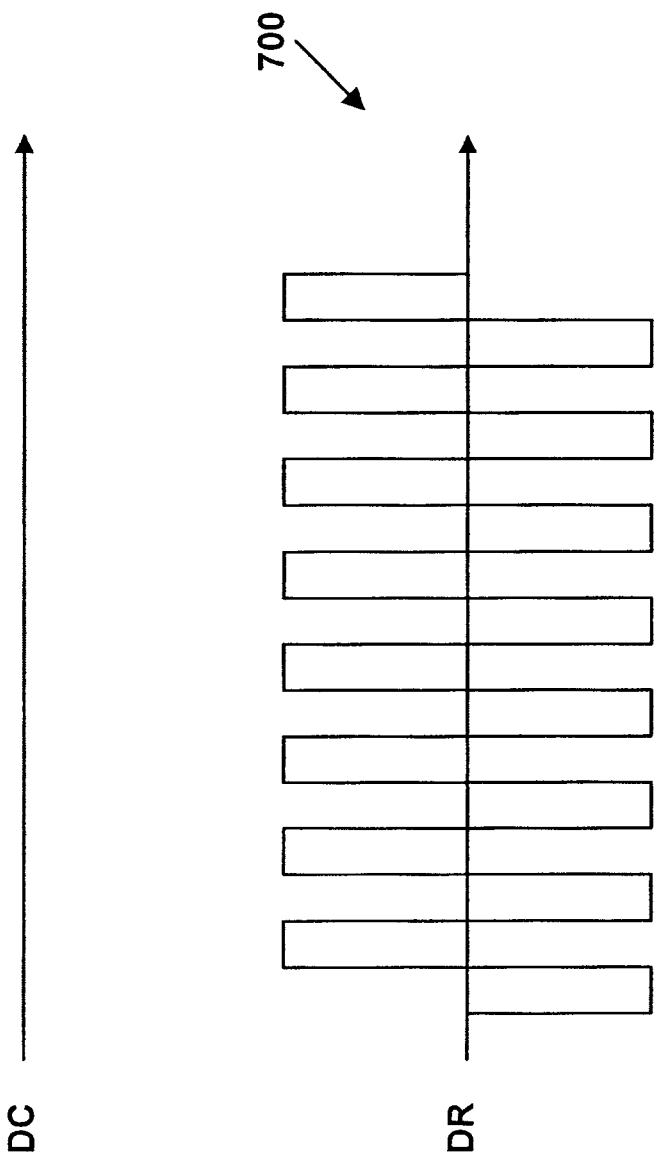
FIG. 7 is a schematic depiction of an example high frequency (HF) blocking signal applied to the dorsal root in accordance with an embodiment of the present disclosure.

In a representative second treatment process for administering therapy for chronic pain management, an HF blocking signal is applied to one or more dorsal roots DR and/or dorsal root ganglion(s) G of a patient, instead of directly to the dorsal column DC. FIG. 7 is a schematic depiction of an example HF blocking signal 700 applied to the dorsal root DR. Blocking at the dorsal root DR and/or the dorsal root ganglion G facilitates blocking sensation signals associated with one or more select regions of the body. In contrast, blocking at the dorsal column DC generally blocks only tactile and proprioceptive signals, generally at all dermatomes associated with sections of the dorsal column DC located below the blocking electrodes.

Arranging the electrodes (e.g., the electrodes carried by the array 103 shown in FIG. 1 or the electrodes 110 shown in FIG. 2) at the dorsal root DR and/or dorsal root ganglion G can enhance the range and effectiveness of the therapy signals. At such locations, the CSF fluid layer is not as thick as it is at the dorsal column DC, which can allow more current to flow to the spinal region. The CSF fluid layer is thicker closer to the dorsal column DC, which can shunt much of the current before the current reaches the dorsal column DC. By positioning the electrodes away from the dorsal column DC, it is expected that an electrical block of the nerve fibers may be established with less power.

In addition, sensory nerve responses typically proceed through the dorsal roots DR to the dorsal column DC, whereas motor nerve responses proceed through the ventral roots VR (see FIG. 3) to the spinal cord SC. Applying therapy signals to the dorsal root DR, therefore, can facilitate blocking of sensory responses (e.g., pain) without decreasing or eliminating the transmission of motor control impulses.

3. Blocking at Peripheral Nerves

In a third treatment process for administering therapy for chronic pain management, an HF blocking signal can be applied to the peripheral nerves of the patient (e.g., the nerves distal of the spinal cord SC). For example, an HF blocking signal can be applied to the somatic nerves of the patient. In another embodiment, the HF blocking signal can be applied to the autonomic nerves of the patient. Applying the HF block to the peripheral nerves can enable placement of the electrodes away from the spinal cord SC and the spinal fluid, and can therefore reduce the likelihood for interference with spinal function.

4. Combining Blocking with Stimulation Therapy

Other treatment processes for administering therapy for chronic pain management combine the application of an HF blocking signal with the process of applying an LF stimulating signal to the dorsal column DC of the patient to induce paresthesia. In general, the HF blocking signal can facilitate the inducement of paresthesia by alleviating patient discomfort resulting from the application of the LF stimulation signal.

The application of an LF stimulation signal to the dorsal column DC can induce paresthesia and/or induce patient discomfort, depending on the distance between the electrode(s) and the spinal cord (e.g., the thickness of the intermediate cerebral spinal fluid layer). As used herein, the term "discomfort" refers generally to an unpleasant, undesirable, uncomfortable and/or unwanted sensation or other response. The term includes, but is not limited to, pain. Typically, in conventional SCS treatment, patient discomfort results from the inadvertent application of the electric field produced by the electrode(s) to an adjacent dorsal root DR. In general, the greater the distance between the electrode and the spinal cord, the greater the likelihood that the electric field will interact with the dorsal root DR to stimulate pain sensations on the dorsal root DR, thus causing discomfort and/or pain as the signal amplitude is increased.

Figure 8:
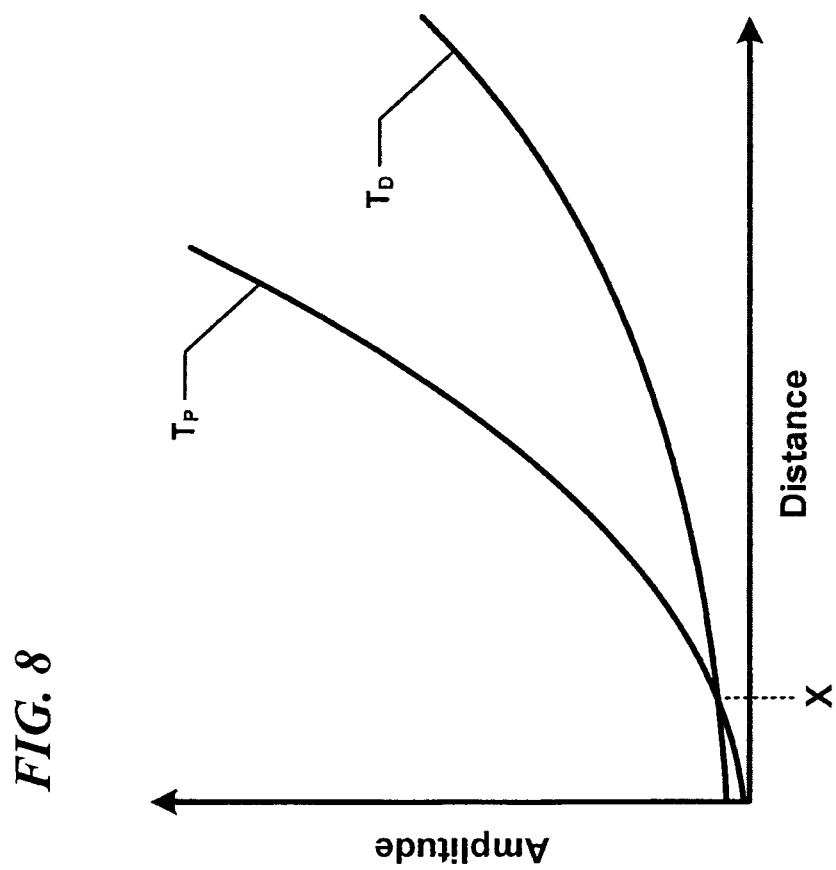
FIG. 8 schematically depicts the amplitude of an example low frequency (LF) stimulation signal likely to induce paresthesia, and the amplitude of the LF stimulation signal likely to induce patient discomfort at a given electrode spacing in accordance with an embodiment of the present disclosure.

FIG. 8 schematically depicts the amplitude of an LF stimulation signal likely to induce paresthesia (represented by threshold curve $T_P$) and the amplitude of the LF stimulation signal likely to induce patient discomfort (represented by threshold curve $T_D$) as a function of spacing between the electrodes and the spinal cord. FIG. 8 is not intended as an exact plot of amplitude as a function of the spacing, but rather is intended to illustrate the general relationship amongst the paresthesia threshold $T_P$, the patient discomfort threshold $T_D$, and the spacing.

As shown in FIG. 8, when the electrodes are spaced relatively close to the spinal cord (e.g., when the spacing is less than about distance X), the electric field created by the electrode(s) induces paresthesia before causing discomfort. However, when the electrodes are spaced farther from the spinal cord (e.g., when the spacing is greater than about distance X), the LF stimulation signal can stimulate the dorsal root DR fibers, thereby potentially causing discomfort, before stimulating the dorsal column fibers at a level sufficient to induce paresthesia. The paresthesia threshold $T_P$ and the patient discomfort threshold $T_D$ cross at the electrode spacing distance X, which is approximately 2 mm in at least some embodiments, and can vary depending on factors that include signal delivery parameters. Further details regarding the relationship amongst electrode spacing, paresthesia, and pain can be found, e.g., in *Effectiveness of Spinal Cord Stimulation in the Management of Chronic Pain: Analysis of Technical Drawbacks and Solutions* by Jan Holsheimer (Neurosurgery, Vol. 40, No. 5, May 1997), the disclosure of which is hereby incorporated herein by reference in its entirety.

Some combination treatment processes in accordance with embodiments of the disclosure for administering therapy for chronic pain management use an HF blocking signal to inhibit the discomfort sensation produced when the LF signal amplitude reaches the discomfort threshold $T_D$, thereby enabling the amplitude of the LF signal to be increased further to the paresthesia threshold $T_P$. This in turn can allow the LF signal to be effective, even if it is provided by an electrode that would otherwise be too far away from the target nerve region (e.g., the dorsal column) to produce paresthesia without also producing discomfort. Other combination treatment processes augment the pain relief provided by paresthesia with the pain relief provided by blocking different sections of the spinal region, as will be discussed later.

a. Blocking at Dorsal Root

Figure 9:
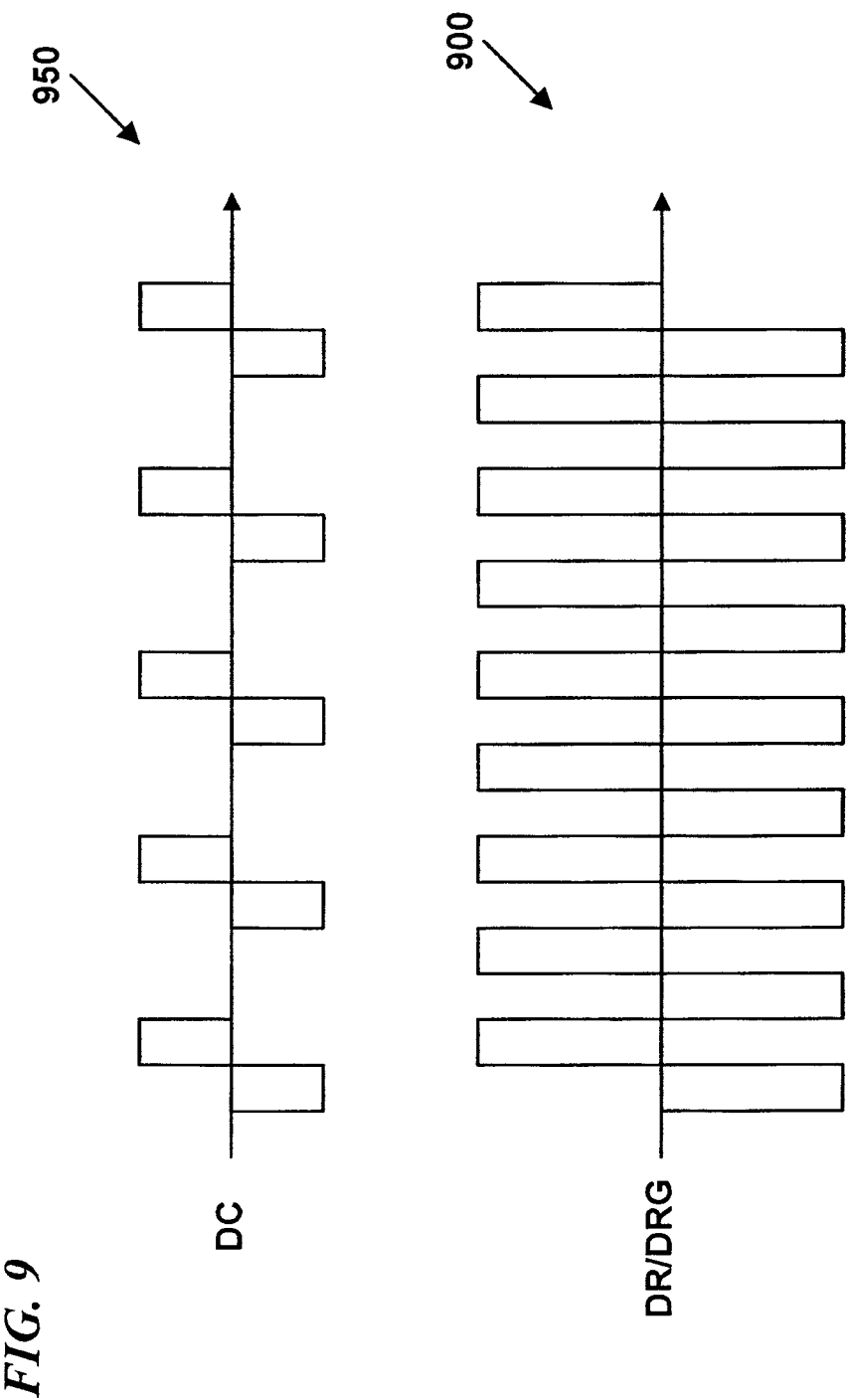
FIG. 9 is a schematic view of an HF blocking signal applied to the dorsal root of a patient and an LF stimulating signal applied to the dorsal column in accordance with an embodiment of the present disclosure.

A representative fourth treatment process for administering therapy for chronic pain management applies an HF blocking signal to the dorsal root DR (and/or dorsal root ganglion G) while applying the LF stimulating signal at the dorsal column DC. As used herein, the term "dorsal root" can include the dorsal root itself, the dorsal root entry region, and the conus. FIG. 9 is a schematic illustration of an HF blocking signal 900 applied to the dorsal root DR of a patient, and an LF stimulating signal 950 applied to the dorsal column DC. The HF signal can establish a block on the dorsal root DR that inhibits the transmission to the brain of pain sensations induced by the electric field of the LF stimulation signal.

In some embodiments, the HF blocking signal 900 is applied to the dorsal root DR prior to application of the LF stimulating signal 950 to the dorsal column DC. In other embodiments, however, the HF blocking signal 900 can be applied at generally the same time as or after the LF stimulating signal 950 is applied to the dorsal column DC. In one embodiment, the LF stimulation signal 950 can be initiated with a low-level amplitude that is subsequently ramped up to a suitable operating amplitude.

In other embodiments, the HF blocking signal applied to the dorsal root DR augments the pain relief provided by the paresthesia. For example, blocking the dorsal root DR is expected to block peripheral pain (e.g., any peripheral pain) from being transmitted through the dorsal root DR. This can include not only discomfort caused by the LF signal, but also the pain that the LF signal is expected to address.

b. Blocking at Dorsal Column

A representative fifth treatment process for administering therapy for chronic pain management applies an HF blocking signal at a first section of the dorsal column DC while applying the LF stimulating signal at a second section the dorsal column DC. The LF stimulating signal is expected to induce a sensation of paresthesia in dermatomes (e.g., all dermatomes) associated with the second section of the dorsal column DC and lower sections (e.g., all lower sections). The HF blocking signal is expected to block excitatory responses produced at the first section and lower sections from reaching the brain.

In some embodiments, the HF blocking signal is applied to the dorsal column DC prior to application of the LF stimulating signal to the dorsal column DC. In other embodiments, however, the HF blocking signal can be applied at substantially the same time as or after the LF stimulating signal is applied. In one embodiment, the LF stimulation signal can be initiated with a low-level amplitude that is subsequently ramped up to a suitable operating amplitude.

In other embodiments, the HF blocking signal applied to the dorsal column DC augments the pain relief provided by the paresthesia. For example, the LF stimulating signal can boost nerve responses that inhibit the sensation of pain and the HF blocking signal can inhibit nerve responses that transmit pain signals to the brain.

In general, the HF signal can be applied to the dorsal column DC above (superior) or below (inferior) the site at which the LF signal is applied. Signals applied to the dorsal column DC will tend to induce action potentials in both directions along the target sensory signal route, e.g., toward the brain (orthodromic) and away from the brain (antidromic). If the orthodromic LF signal creates a pleasant (or at least non-objectionable) sensation, such as tingling, that masks the target pain, then there may be no need for an HF signal applied to the dorsal column DC. However, if the LF signal creates an unpleasant sensation (an orthodromic signal), and the corresponding antidromic signal acts to mitigate the target pain, then an HF signal may be applied superior to the LF stimulation site to suppress the unpleasant sensation caused by the orthodromic signal, while having no effect on the beneficial antidromic signal. Accordingly, the patient can be outfitted with a device that includes an LF signal generator coupled to electrical contacts at the dorsal column, and an HF signal generator coupled to electrical contacts located superiorly on the dorsal column DC. In particular embodiments, the HF signal generator is activated if (a) the paresthesia created by the LF signal is objectionable to the patient, and (b) the antidromic action potentials created by the LF signal reduce the target pain.

In another embodiment, the HF signals can be applied to the dorsal column DC at a location inferior to where the LF signals are applied. In this case, it is assumed that the antidromic signals produced by the LF signals do not contribute (or do not contribute significantly) to reducing the target pain. Accordingly, applying HF signals at an inferior location, which is expected to block such antidromic signals, is not expected to impact the effectiveness of the LF signals, e.g., the orthodromic paresthesia effect. It is further assumed, based on recent evidence, that dorsal column DC fibers transmit pain, in contrast to more traditional models which posit that pain travels through the spinothalamic tract. Based on this assumption, blocking orthodromic pain signals passing along the dorsal column is expected to reduce the target pain.

B. Treatment Parameters

In general, the therapy systems 100, 200 (FIGS. 1 and 2) can be utilized to provide chronic pain management to patients using one of the above described therapy options, or one or more combinations thereof. The following treatment parameters are representative of treatment parameters in accordance with particular embodiments.

1. Signal Parameters

In general, HF blocking signals can have a frequency ranging between about 2,500 Hz and about 100,000 Hz. In a particular embodiment, the HF blocking signal has a frequency ranging between about 2,500 Hz and about 20,000 Hz and in another particular embodiment, between about 3,000 Hz and about 10,000 Hz. In other particular embodiments, the HF signal has a frequency of greater than 10,000 Hz. Frequencies above 10,000 Hz may result in shorter transition times, e.g., shorter times required to establish a block. The current of the HF blocking signals generally can range from about 2 mA to about 20 mA. In a particular embodiment, the current of a representative HF blocking signal is about 5-10 mA.

2. Modulating Signal Amplitude After Initialization

After an HF blocking signal has been initialized, the amplitude of the blocking signal can be reduced from a first operating level to a second, lower operating level without affecting the sensory experience of the patient. For example, in particular embodiments, the amplitude of the HF blocking signal can be reduced by about 10-30% after initialization without affecting the established block. Such a result can advantageously decrease the amount of power required to operate the therapy system 100, 200 (FIGS. 1 and 2). For example, decreasing the operating power can increase the battery life of the pulse generator 101 or otherwise decrease the drain on the power source.

3. Modulation of On/Off Time

In certain embodiments, therapy can be applied in a discontinuous fashion so as to include periods when the therapy is applied, and periods when the therapy is terminated according to a duty cycle. In different embodiments, therapy application periods can range from a few seconds to a few hours. In other embodiments, the duty cycle of a therapy signal can extend over a few milliseconds.

C. Initializing Blocking Signals

When HF blocking signals are initially applied to nerve fibers, the patient can experience an onset response before the block takes effect. An onset response is induced by a brief activation of the nerve fibers resulting in sudden pain and/or involuntary muscle contractions. Such an onset response can occur regardless of whether the therapy signals are applied to the dorsal column DC, the dorsal root DR, the dorsal root ganglions G, or to the peripheral nerves of the patient.

In order to alleviate these symptoms, various initialization procedures can be used as described below. For example, the nerve activation caused by initializing the blocking signal can be mitigated by adjusting the signal parameters (e.g., amplitude and/or frequency) of the blocking signal. Alternatively, patient discomfort caused by the onset response can be masked by applying additional pain management therapy.

1. Mitigating an Onset Response

As the term is used herein, mitigation of an onset response refers generally to a decrease in the otherwise resulting activation of the nerve to which the blocking signal is being applied.

a. Amplitude Ramp-Up

A first initialization procedure for mitigating patient onset response includes gradually ramping up the amplitude of the blocking signal being applied to the nerve. As the term is used herein, the amplitude of the blocking signal can refer to the current amplitude and/or the voltage amplitude of the signal since a direct relationship exists between the current and the voltage of the blocking signal.

By starting the signal at a lower amplitude, fewer nerve fibers are affected and stimulated initially. As the amplitude is increased, additional nerve fibers are stimulated as the block is established at the previous nerve fibers. The total number of nerve fibers activated at any one time, therefore, is decreased when compared with an un-ramped initialization. Patient discomfort that may be caused by the stimulated fibers is likewise expected to be mitigated.

Figure 10:
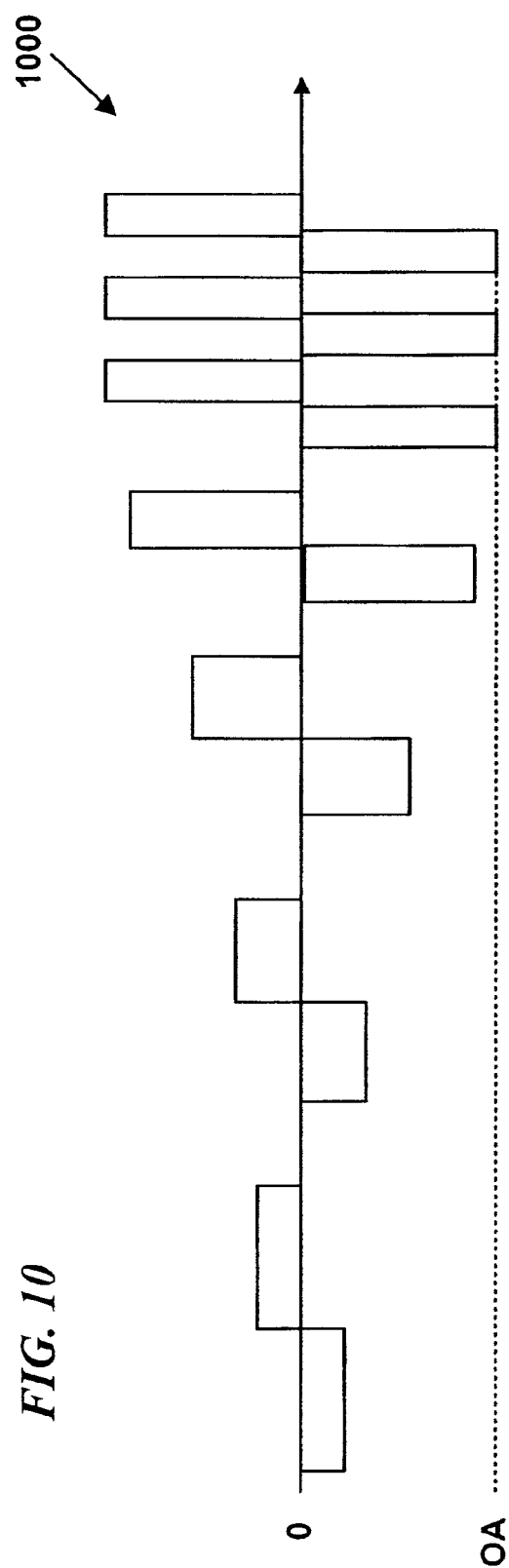
FIG. 10 is a schematic diagram of an example blocking signal, which has an amplitude that is gradually increased to an operating amplitude over a finite period of time in accordance with an embodiment of the present disclosure.

For example, in FIG. 10, the amplitude and/or frequency of representative blocking signal 1000 is gradually increased to an operating amplitude OA over a finite period of time. In one embodiment, the amplitude of the waveform 1000 is increased over a period of a few seconds. In other embodiments, however, the amplitude and/or frequency can be increased over a greater or lesser period of a time (e.g., a few minutes or a few milliseconds). In still further embodiments, the amplitude and/or frequency can be decreased over time, as is discussed further below with reference to FIGS. 11A-11C.

b. Amplitude and Frequency Modulation

Figure 11A:
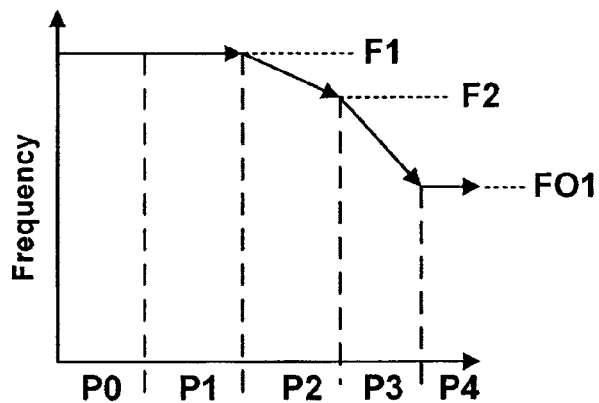
FIG. 11A is a schematic graph generally showing the changes in frequency during application of a therapy in accordance with an embodiment of the present disclosure.
Figure 11B:
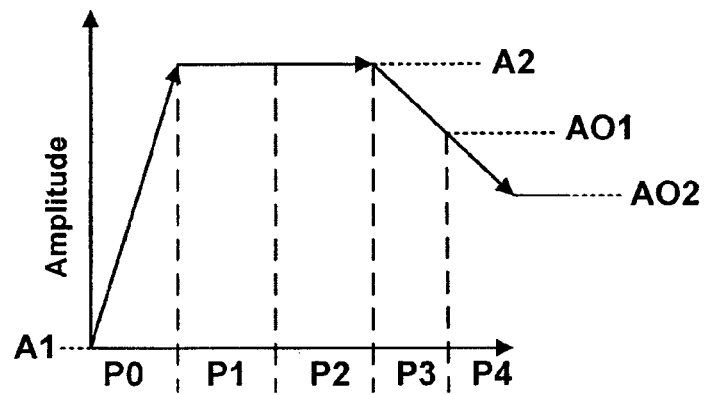
FIG. 11B is a schematic graph generally showing the changes in amplitude during application of the therapy of FIG. 11A in accordance with an embodiment of the present disclosure.
Figure 11C:
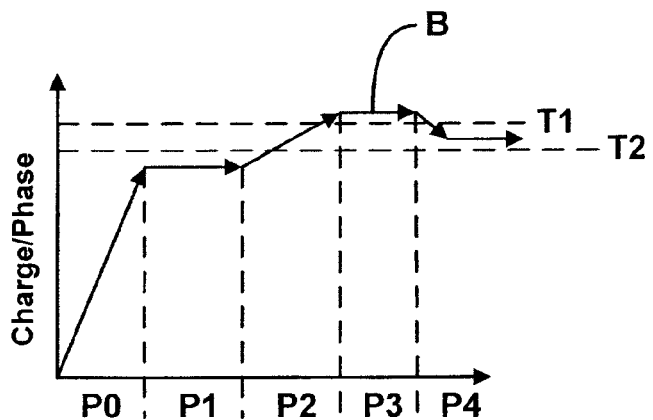
FIG. 11C is a schematic graph generally showing the changes in charge/phase during application of the therapy of FIG. 11A in accordance with an embodiment of the present disclosure.

Referring to FIGS. 11A-11C, a second initialization procedure for reducing the onset response to treatment can include at least two phases, one in which the applied frequency and/or amplitude are above general operating levels, and one in which the frequency and/or amplitude are reduced to operating levels. These phases, as well as additional (and in some cases, optional) phases are described below.

In some embodiments, the second initialization procedure can include an optional onset phase P0 during which the frequency of the blocking signal is maintained at a constant level F1 (see FIG. 11A) and the amplitude of the blocking signal is ramped up from a low amplitude A1 to a high amplitude A2 (see FIG. 11B).

In a first phase P1, a blocking signal having a frequency F1 and amplitude A2 greater than the general operating frequency F01 and operating amplitude A01 is applied to a nerve. For example, a blocking signal having a frequency in the range of about 2,500 Hz to above 20 KHz and an amplitude up to about 20 mA can be applied during the first phase P1.

In some embodiments, the application of the blocking signal having a very high frequency F1 and a high amplitude A2 rapidly results in a block on the nerve. In other embodiments, however, the second initialization procedure can include an optional transition phase P2 during which a block is established (i.e., during which the signal increases in strength above the threshold T1). Even when the transition phase P2 is utilized, however, the blocking signal establishes a block on the nerve more rapidly than would a signal that simply has the operating frequency and operating amplitude.

During the transition phase P2, the frequency of the blocking signal is decreased from the very high frequency F1 to a frequency F2 (see FIG. 11A). Frequency F2 is lower than frequency F1, but still significantly higher than the operating frequency FO. Decreasing the frequency increases the charge per phase and hence the strength of the blocking signal (see FIG. 11C). The frequency is lowered until the signal strength crosses the blocking threshold T1. In one embodiment, the amplitude may be further increased as well during the transition phase P2.

In a subsequent phase P3, the frequency and amplitude of the blocking signal can be reduced from a level at which the block is established to first operating levels (e.g., FO1, AO1 shown in FIG. 11B). In one embodiment, a block is established when the charge per phase of the blocking signal passes above a blocking threshold T1 (see FIG. 11C). Decreasing the amplitude of the blocking signal lessens the drain on the power source. Decreasing the frequency increases the charge per phase (e.g., the stimulation applied to the nerve fibers) to compensate for the reduction in amplitude. In one embodiment, a practitioner begins ramping down the frequency and the amplitude concurrently. In other embodiments, however, the amplitude and frequency can be ramped down at different times.

In some embodiments, an optional phase P4 includes decreasing the amplitude of the signal from the first operating level A01 to a different operating level A02 after the block is established (see FIG. 11B). Decreasing the amplitude lowers the charge per phase (see FIG. 11C). The block can be maintained, even if the charge per phase drops below the first threshold T1, as long as the charge per phase does not drop below a second threshold T2 (see FIG. 11C). Typically, threshold T2 is 10-30% less than the threshold T1.

Figure 12:
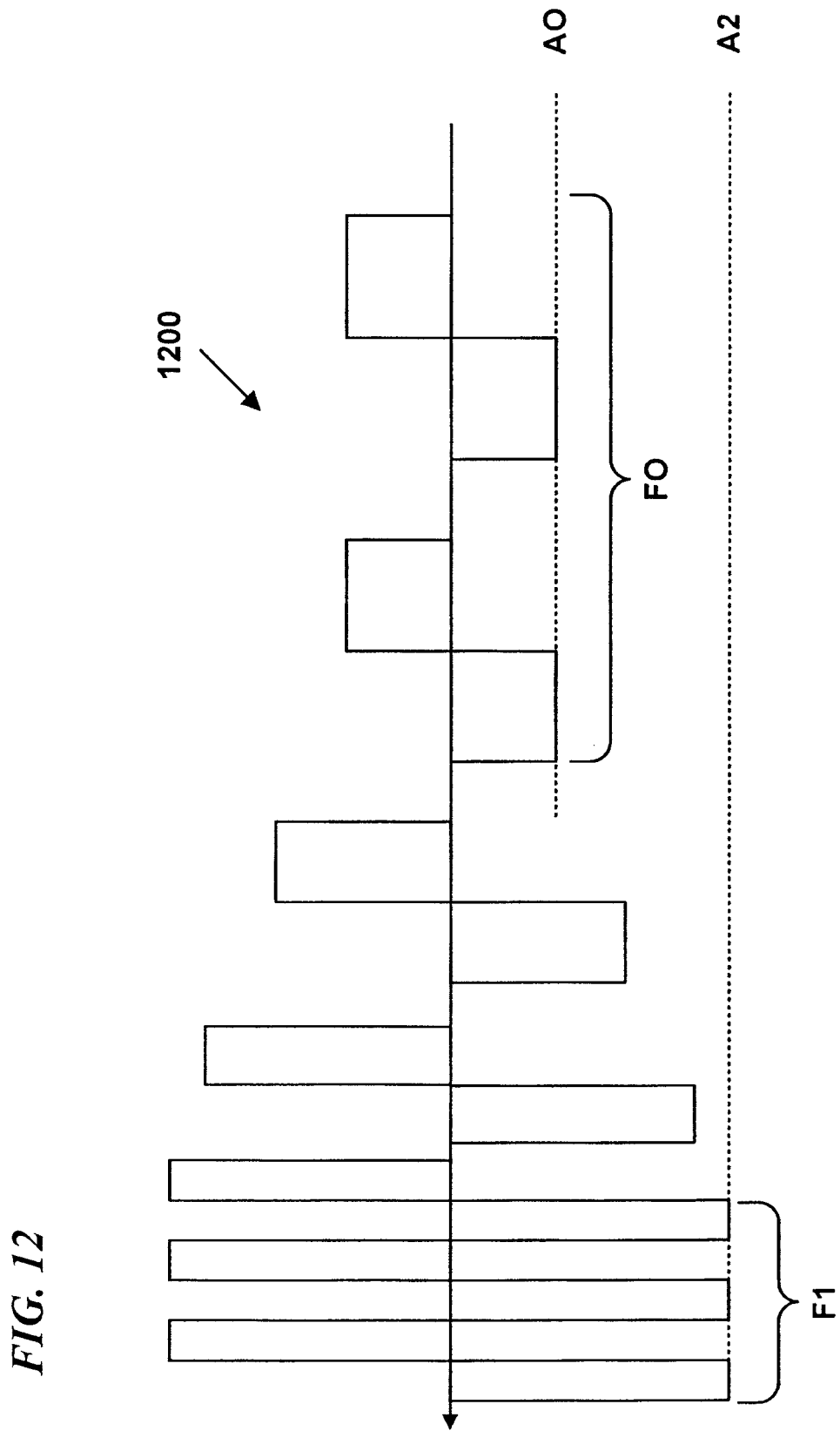
FIG. 12 is a schematic depiction of an example blocking signal initially having a high frequency (e.g., about 30-50 KHz) and a high amplitude (e.g., about 15-20 mA) in accordance with an embodiment of the present disclosure.

FIG. 12 is a schematic depiction of an example blocking signal 1200 initially having a high frequency F1 (e.g., about 30-50 KHz) and a high amplitude A2 (e.g., about 15-20 mA). In the example shown, the blocking signal 1200 is a biphasic, charge balanced, square waveform. In other embodiments, however, the blocking signal 1200 can include any desired waveform. When the block on the nerve is established, the amplitude of the blocking signal 1200 is ramped down to an appropriate operating level AO (e.g., about 5-10 mA). As further shown in FIG. 12, the frequency of the blocking signal 1200 also can be decreased to an appropriate operating level FO (e.g. about 3-10 KHz).

Figure 13:
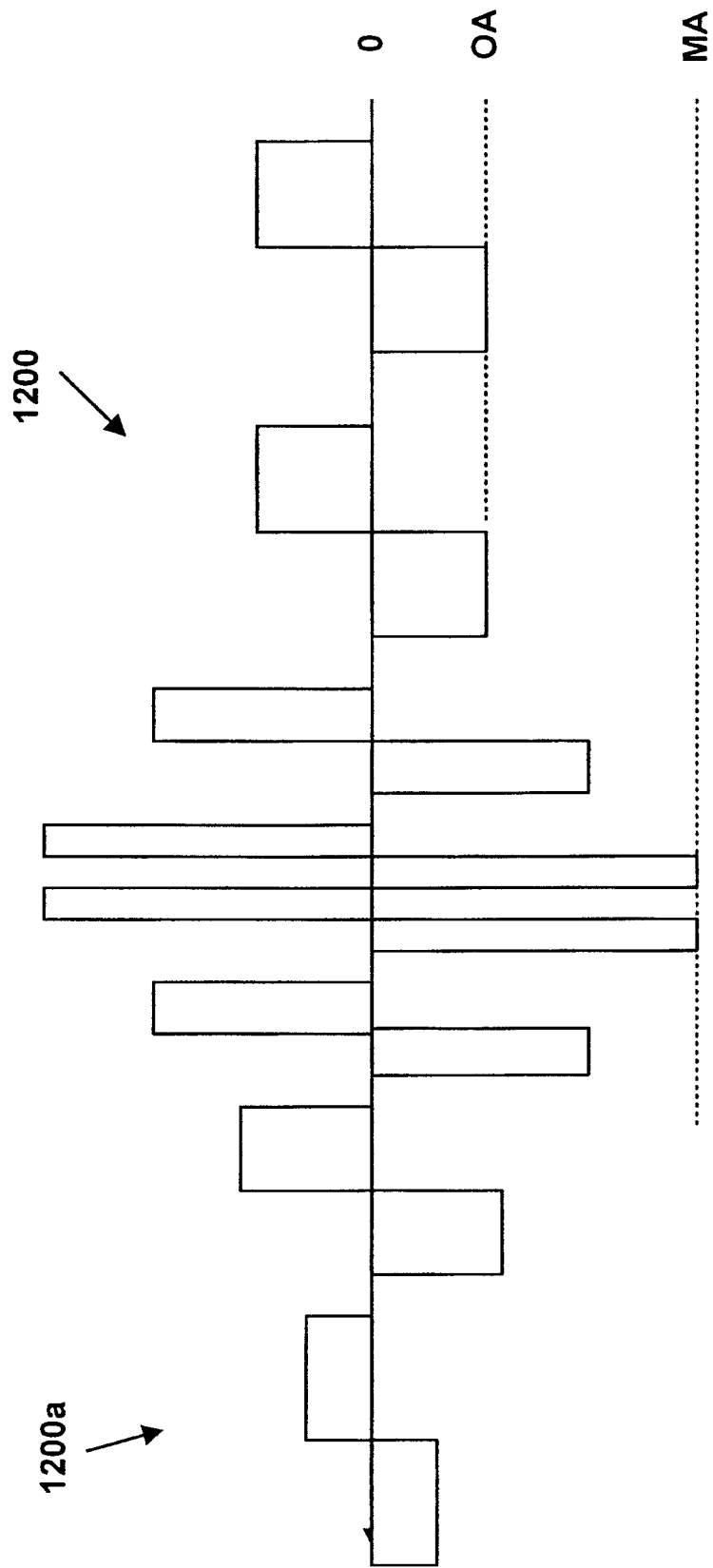
FIG. 13 shows the blocking signal of FIG. 12 with an initial ramp-up period in accordance with an embodiment of the present disclosure.

FIG. 13 shows the blocking signal 1200 having an initial ramp-up period shown at 1200a, during which the signal amplitude is increased to a maximum amplitude MA. Ramping up the amplitude of the signal can allow the signal to be initiated safely with reduced or non-existent patient discomfort. In other embodiments, however, the onset phase P0 can be skipped and the very high amplitude A2 of the blocking signal can be applied from the beginning.

2. Masking Onset Response

As the term is used herein, masking of an onset response refers generally to a decrease in the discomfort of the patient otherwise resulting from an onset response, without affecting activation of the nerve to which the blocking signal is being applied.

a. Inducing Paresthesia

Figure 14:
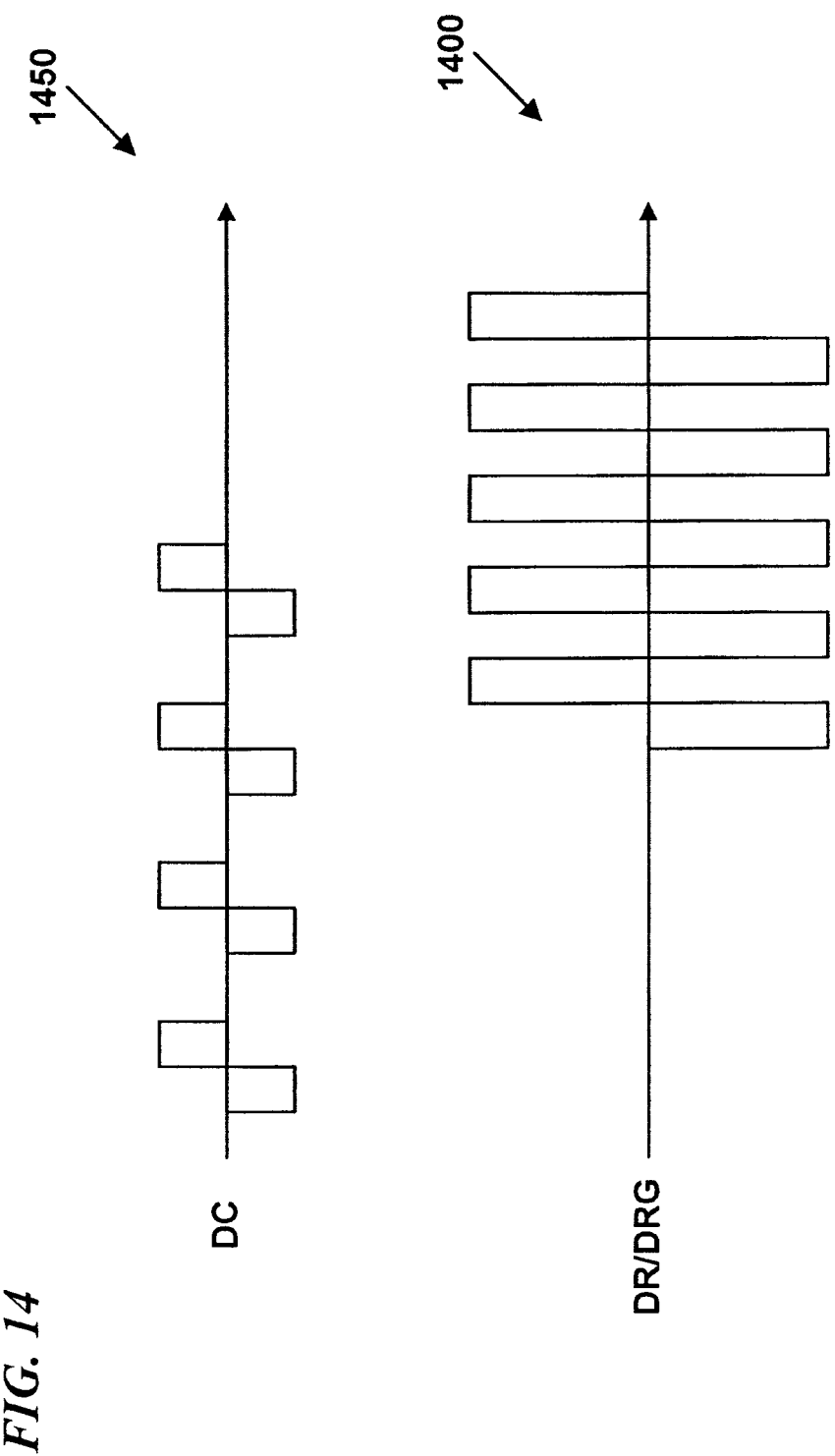
FIG. 14 is a schematic depiction of an example LF signal and an example HF signal indicating a representative timing strategy for applying the LF and HF signals in accordance with an embodiment of the present disclosure.

Referring to FIG. 14, paresthesia induced by an LF stimulating signal applied to the dorsal column DC can mitigate the onset response of an HF blocking signal applied to the dorsal root DR. The low-level paresthesia, while not strong enough to control the chronic pain of the patient, can alleviate some or all of the discomfort experienced by the patient as a result of the initialization of the HF blocking signal. Examples of the relative timing for the therapy signals are shown in FIG. 14.

As shown in FIG. 14, an LF stimulating signal 1450 having a low amplitude and a low frequency (e.g., in the range of about 40 Hz to about 250 Hz) is applied to the dorsal column DC of a patient to induce paresthesia. Next, an HF blocking signal 1400 having a high frequency (e.g., ranging from about 2,500 Hz to about 100,000 Hz, and in a particular embodiment, from about 2,500 Hz to about 20,000 Hz, and in a further particular embodiment, about 2,500 Hz to about 10,000 Hz) is applied to the dorsal root DR of the patient. The paresthesia induced by stimulating the dorsal column DC can enhance patient comfort while the partial or complete HF block is established at the dorsal root DR. In a representative example, an LF signal is applied to the dorsal column DC for a period of several seconds before applying the HF signal, at least up to an amplitude below that which causes discomfort and/or pain. In particular embodiments (e.g., in cases for which the HF blocking signal by itself has a sufficient therapeutic effect), the LF signal can be halted once the HF signal is established and the period for experiencing an onset response has passed. In a representative embodiment, this time period can be from about 5 seconds to about 5 minutes. The LF signal can then be re-established for a short period the next time an HF signal is initiated to again reduce or eliminate the onset response. In this manner, the onset response can be controlled without requiring a continuous (and therefore power consuming) LF signal. This arrangement can be used when the LF signal is applied at a location superior to the HF signal location, e.g., when both the LF and HF signals are applied to the dorsal column DC, or when the LF signal is applied to the dorsal column DC above a dorsal root DR location at which the HF signal is applied.

b. Pharmacological Anesthetic

One or more pharmaceutical drugs affecting the pain neural transmission synapse or neuromuscular junction also can be given to the patient prior to initiating a therapy signal, such as an HF blocking signal. For example, bupivacaine and/or other suitable local anesthetics may be used in this regard, when injected epidurally. The various classes of analgesics used for epidural and spinal block include local anesthetics, opioids, adrenergic agonists, and cholinergic agonists. Local anesthetics inhibit neural conduction by reversibly blocking conductance in axonal sodium channels. Opioids exert their effect by reversibly binding to opioid receptors in the dorsal horn of the spinal cord. Alpha-2 adrenergic agents interact with alpha-2 adrenergic receptors in the spinal cord, and cholinergic agonists produce analgesia by increasing the concentration of acetylcholine proximate to muscarinic and nicotinic receptors in the superficial layers of the dorsal horn of the spinal cord. The pharmacological agent can be delivered via the same device that supplies the electrical signals, or the agent can be delivered via a separate device. In a particular embodiment, PLGA or another suitable polymer can be used to exude the agent.

D. Electrode Configurations

FIGS. 15-18 illustrate different design variations that include an electrode array having four electrodes. In other embodiments, arrays can include a greater or lesser number of electrodes arranged in the same or other patterns. In a particular embodiment, an array can contain two electrodes. In another embodiment, an array can contain three electrodes. In yet another embodiment, an array can contain up to sixteen or more electrodes. Increasing the number of electrodes increases the number of channel vectors which can be utilized during therapy, thereby broadening the types of therapy applied and/or the regions over which the therapy is applied.

Figure 15:
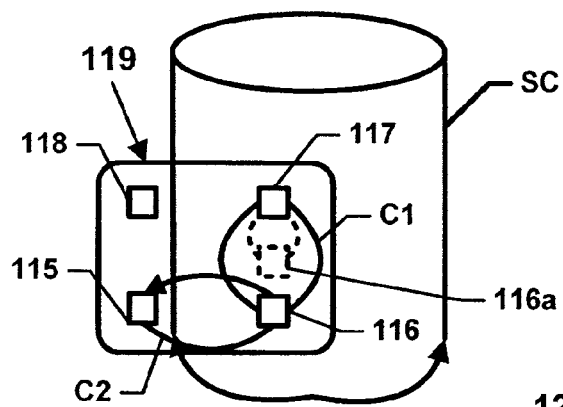
FIGS. 15-18 are schematic block diagrams of representative electrode arrays including four electrodes implanted at the spinal cord of a patient in accordance with an embodiment of the present disclosure.

FIG. 15 illustrates an example electrode array 119 including four electrodes 115, 116, 117, 118 implanted at the spinal cord SC. In the embodiment shown in FIG. 15, a first therapy signal (e.g., for affecting paresthesia at the dorsal column DC) is applied via a first output channel C1 (shown schematically) of the array 119 that extends along the dorsal column DC and can include a first pair of electrodes 116, 117. A second therapy signal (e.g., for blocking pain in the dorsal root DR) is transmitted via a second output channel C2 (shown schematically) of the array 119 that extends at an angle (e.g., 10°, 30°, 60°, 90°, 120°, etc.) to the first output channel C1 and can include a second pair of electrodes 115, 116.

In such a configuration, the vector of the electrical stimulation applied via the first channel C1 between electrode 116 and electrode 117 is angled relative to the vector of the electrical stimulation applied through the second channel C2 between electrode 116 and electrode 115. By arranging the electrodes to provide angled (e.g., orthogonal) signal channels C1, C2, electric field interaction between the channels C1, C2 can be reduced or minimized. Furthermore, the first channel C1 can be oriented to align with the dorsal column DC and the second channel C2 can be oriented to align with the dorsal root DR. For example, the second channel C2 can be arranged generally orthogonal adjacent the thoracic region of the spine, and more acutely angled closer to the lumbar region.

The remaining electrode 118 can be used to create other channels for applying therapy signals. For example, if the dorsal root crosses the electrode array 119 above the second pair of electrodes 115, 116, then the second therapy signal can be applied along a third channel (not shown) between electrodes 117, 118 to block the dorsal root DR. In other embodiments, the remaining electrode 118 can provide other stimulation vectors for the dorsal column DC to further optimize the therapy.

The foregoing arrangement, in which one of the first electrodes (e.g., first electrode 116) forms part of both the first channel C1 and the second channel C2 can be suitable when the signals applied to both channels C1, C2 are interlaced. For example, this arrangement can be suitable when an HF signal applied to the second channel C2 has a duty cycle of less than 50%, and an LF signal applied to the first channel C1 is interlaced with the HF signal. In another arrangement (shown in dashed lines in FIG. 15), an additional first electrode 116a is used in combination with the electrode 117 for the first channel C1, and electrodes 115, 116 form a separate second channel C2. This arrangement can be used when the duty cycle applied to one or both channels C1, C2 is 50%. Though not shown for purposes of clarity, a similar arrangement can be applied to the embodiments shown in other Figures as well, e.g., FIGS. 16 and 18.

a. Lateral Spacing

Figure 16:
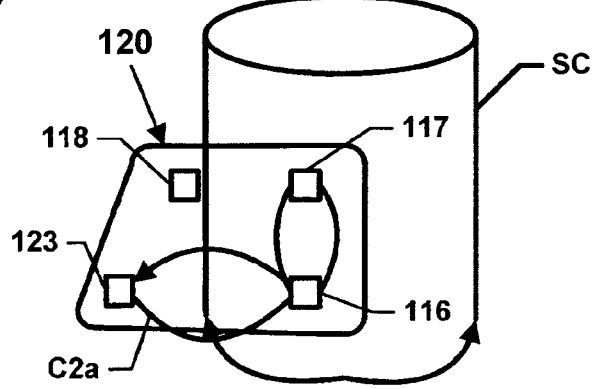
Figure 17:
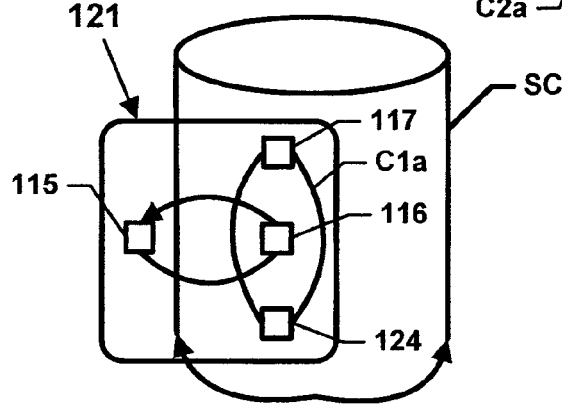
Figure 18:
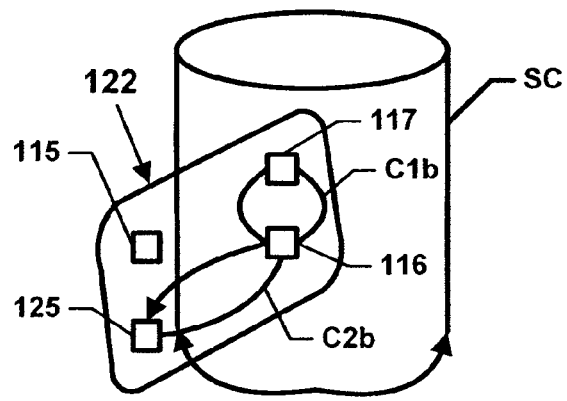

FIG. 16 shows an electrode array 120, which is a variant of the electrode array 119 shown in FIG. 15. The electrode array 120 includes an electrode 123 that is laterally offset from the corresponding electrode 115 shown in FIG. 14 and accordingly forms a second output channel C2a having an increased length. The increased length of the channel C2a produces an electric field having a wider coverage. In specific patient anatomies, an increased field can be advantageous, for example, when it is desirable to block an increased number of fibers. In general, the larger the electric field, the greater number of nerve fibers affected by the therapy signal. When applied along the dorsal column DC, a large electric field penetrates deeper and more laterally into the dorsal column DC, thereby inhibiting pain over a large region of the body (e.g., by covering multiple dermatomes).

However, as noted above, it is not always desirable to affect large regions of nerve fiber. For example, a larger electric field applied to the dorsal column DC may be more likely to "leak" to adjacent fibers on the dorsal root DR or ventral root. In addition, a larger electric field can stimulate or block fibers carrying motor control impulses (e.g., ventral roots). Large electric fields can be more likely to affect these motor nerve fibers and cause undesirable side effects to the treatment. Accordingly, in at least some such instances, the array 119 shown in FIG. 15 may be more appropriate.

b. Axial Spacing

Electrodes within an electrode array also can be axially spaced to increase the penetration along the dorsal column DC. For example, in an arrangement shown in FIG. 17, an electrode array 121 can include an electrode 124 axially aligned with electrodes 116, 117, but arranged in an axially inferior position relative to the electrode 116.

In some embodiments, channels can be formed between non-adjacent electrodes to increase the length of the channels. For example, in the embodiment shown in FIG. 17, the electrode 124 can form a first channel C1a with the electrode 117. In other embodiments, however, channel length is increased by increasing the spacing between adjacent electrodes.

c. Non-Orthogonal Orientation

In certain embodiments, electrode arrays can be configured to provide vectors for electrical stimulation that reflect the anatomy of the patient. For example, an electrode array 122 shown in FIG. 18 includes electrodes 115, 116, 117 that are generally similar to the corresponding electrodes discussed above with reference to the array 119. In addition, the electrode array 122 includes an electrode 125 spaced axially from electrode 115. In the example shown, the electrode 125 is spaced at an axially inferior position relative to electrode 115. Electrode 125 can be included in place of electrode 118 of array 119.

Electrode array 122 can advantageously provide channel vectors (e.g., channel C2b) oriented in directions generally followed by dorsal roots DR leaving the dorsal column DC at the intervertebral foramen of the spinal cord SC. Proximal the brain, the dorsal root DR branches from the dorsal column DC at a generally orthogonal orientation relative to the dorsal column DC. Distal of the brain, however, the dorsal roots DR branch from the dorsal column DC at increasingly downward angles. Accordingly, an array of the type shown in FIG. 18 may be particularly suitable for applications distal of the brain.

3. Percutaneous Lead Configurations

Various details of array electrode configurations are described above. It will be appreciated that many of the same electrode configurations can be achieved by the use of bipolar or multi-polar, percutaneous leads as described in connection with FIGS. 19A-21. Typically, percutaneous leads require less invasive surgery and, therefore, are more convenient to implant than electrode arrays.

a. Bipolar Leads

Figure 19A:
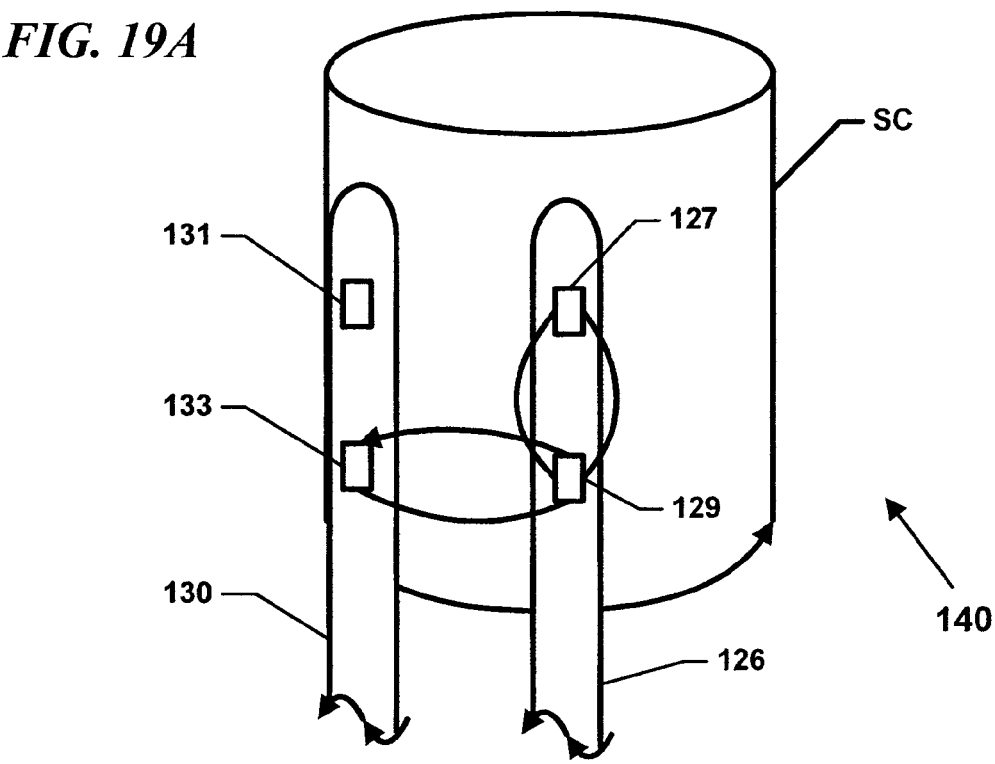
FIG. 19A is a schematic block diagram of a lead configuration in which first and second percutaneous leads are implanted within the patient together in accordance with an embodiment of the present disclosure.

A lead configuration 140, shown schematically in FIG. 19A, includes a first percutaneous lead 126 that is implanted within the patient together with a second percutaneous lead 130. The first percutaneous lead 126 has first and second electrodes 127, 129, respectively, and the second percutaneous lead 130 has first and second electrodes 131, 133, respectively. The electrodes 127, 129, 131, 133 are generally aligned along the spinal cord SC. Typically, the electrodes 127, 129 of the first lead 126 are aligned parallel, but laterally displaced from the electrodes 131, 133 of the second lead 130.

Therapy signals can be generated using one or both leads 126, 130. To apply a therapy signal to the dorsal column DC, the therapy signal is typically generated by electrodes arranged along a single lead (e.g., the first lead 126). To apply a therapy signal to the dorsal root DR, the therapy signal is typically generated by electrodes on two or more different leads (e.g., a first electrode 129 on the first lead 126, and a second electrode 133 on the second lead 130). In the example shown, an LF stimulation signal can be applied to the dorsal column DC via the first lead 126 and an HF blocking signal can be applied to the dorsal root DR via electrodes 129, 133 on the first and second leads 126, 130, respectively.

In other embodiments, other types of therapy signals can be applied via the first and second leads 126, 130. For example, an HF blocking signal can be applied to the dorsal column DC via the electrodes 131, 133 of the second lead 130.

Figure 19B:
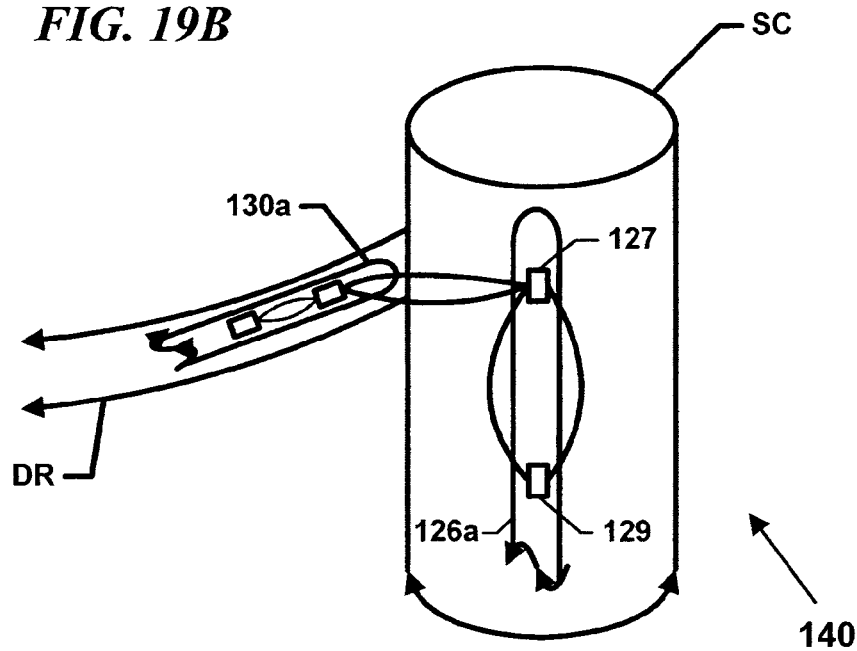
FIG. 19B is a schematic block diagram of a lead configuration in which a first percutaneous lead is implanted within the patient adjacent the dorsal column and a second percutaneous lead is implanted within the patient adjacent the dorsal root in accordance with an embodiment of the present disclosure.

FIG. 19B illustrates another embodiment in which a second lead 130a is positioned along the dorsal root DR and a first lead 126a is positioned along the dorsal column DC (see FIG. 19B). In one aspect of this embodiment, an up-regulating (e.g., paresthesia-inducing) signal can be applied to the first lead 126a at the dorsal column DC and a down-regulating (e.g., blocking) signal can be applied to the second lead 130a at the dorsal root DR.

Figure 19C:
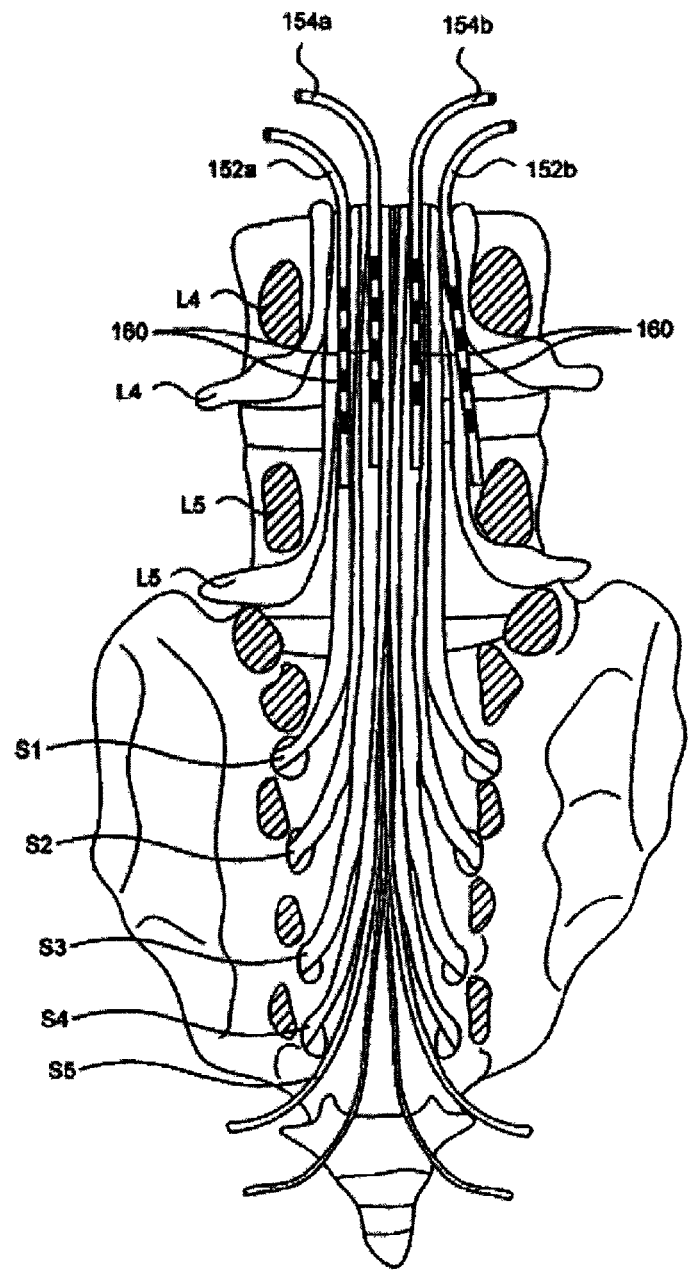
FIG. 19C is a partially schematic illustration of percutaneous leads positioned at lumbar locations in accordance with embodiments of the disclosure.

FIG. 19C illustrates the inferior portion of the spine, including the lower lumbar and sacral vertebrae, and associated nerve roots. Signals (e.g., HF signals) can be applied to these roots alone or in conjunction with signals applied superiorly to the dorsal column. In particular arrangements, leads or pairs of leads can be positioned between adjacent roots to provide signals to a number of roots that is greater than the number of leads. For example, a first pair of leads 152a, 154b, each having electrodes or electrode contacts 160, can be positioned along opposite sides of the S3 root to provide signals to at least the S2, S3 and S4 roots. In another representative example, a second pair of leads 152b, 154b can be placed alongside the L5 root to provide signals to the L5 root, the S1 root and optionally the L4 root. In other embodiments, leads having similar (or other) structures can be placed along other roots. An advantage of the foregoing arrangement is that a reduced number of leads can be used to apply signals to a greater number of roots.

b. Multi-Channel Lead Arrangement

Figure 21:
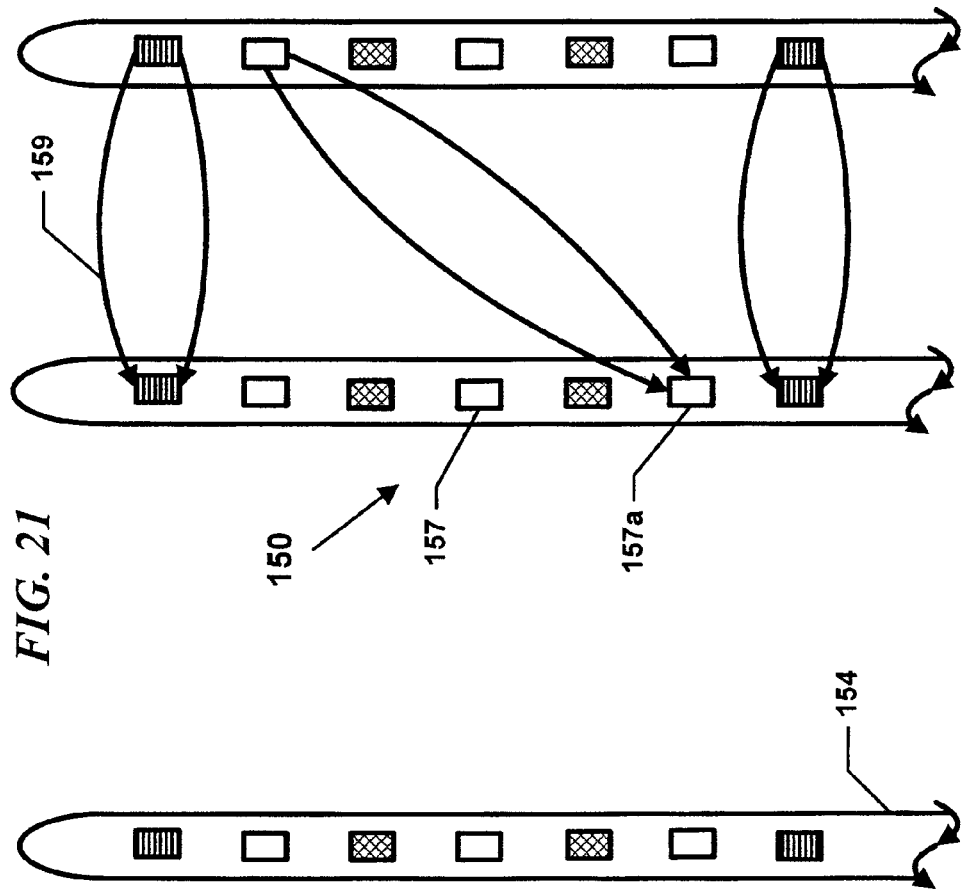
FIG. 21 is a schematic block diagram of a multi-channel, percutaneous lead arrangement having first and second leads configured to deliver multiple therapy signals to a dorsal root of a patient in accordance with an embodiment of the present disclosure.
Figure 20:
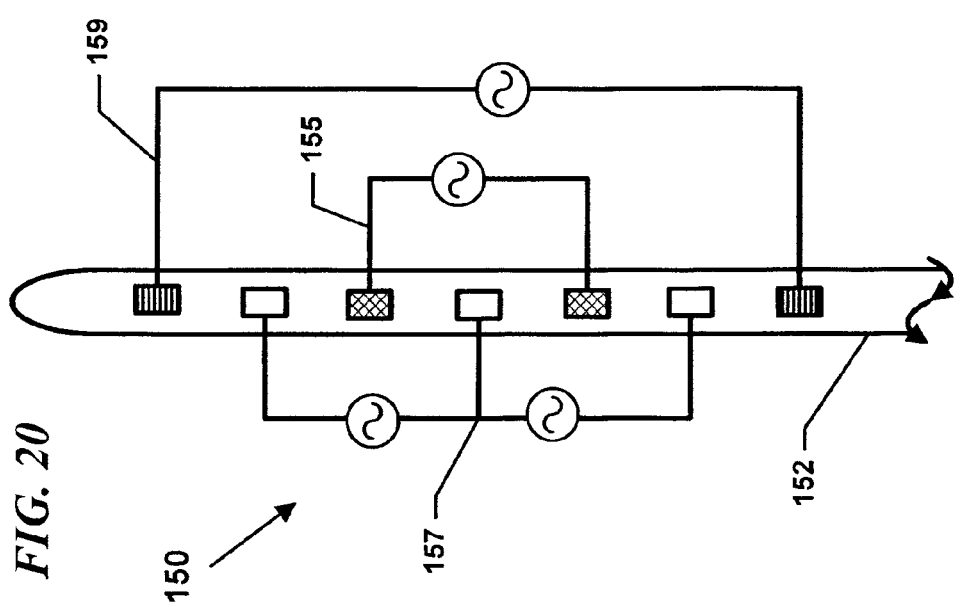
FIG. 20 is a schematic block diagram of a multi-channel, percutaneous lead arrangement having first and second leads configured to deliver multiple therapy signals to a dorsal column of a patient in accordance with an embodiment of the present disclosure.

FIGS. 20 and 21 illustrate a multi-channel, percutaneous lead arrangement 150 having first and second leads 152, 154 configured to deliver multiple therapy signals to a patient. FIG. 20 illustrates how the lead arrangement 150 can be used generally to apply therapy signals to the dorsal column DC. FIG. 21 illustrates how the lead arrangement 150 can be used generally to apply therapy signals to the dorsal root DR. In different embodiments, the leads 152, 154 can cooperate to provide multiple types of therapy signals to the dorsal column DC and/or dorsal root DR of a patient.

Each lead 152, 154 of the lead arrangement 150 includes a first arrangement 155 of electrodes, a second arrangement 157 of electrodes, and a third arrangement 159 of electrodes. In the example shown, the first and third arrangements 155, 159 include bipolar electrodes. The second arrangement 157 includes a tripolar electrode arrangement (e.g., a central cathode with anodes on either side). In such an embodiment, current can be controlled independently to adjust therapy for variations in electrode-to-nerve positioning. In other embodiments, however, the leads 152, 154 can include other arrangements of electrodes. In the example shown, each lead 152, 154 of the lead arrangement 150 includes seven electrodes. In other embodiments, however, a lead can include one, two, three, four, five, or more electrodes.

In general, the first arrangement 155 of electrodes on one or both leads 152, 154 can apply an LF stimulation signal to the dorsal column DC to induce a sensation of paresthesia. Typically, the electric field of the stimulating signal can be generated by electrodes on a single lead so that the electric field is oriented along the length of the dorsal column DC. For example, in FIG. 20, the electrodes of the first arrangement 155 of the first lead 152 create an electric field at the dorsal column DC to induce a sensation of paresthesia.

In one embodiment, the electrodes of the second arrangement 157 of one of the leads 152, 154 can generate an electric field of an HF blocking signal at the dorsal column DC to establish a block on the dorsal column DC. For example, the electrodes of the second arrangement 157 can form a tripolar configuration to produce an HF blocking signal as shown in FIG. 20. In other configurations, the HF blocking signal can be generated using a lesser or greater number of electrodes of the second arrangement 157.

In another embodiment, the HF blocking signal can be applied to a dorsal root DR along at least some of the electrodes of the second arrangement 157 on both leads 152, 154. For example, in FIG. 21, the middle electrodes of the second arrangement 157 on both leads 152, 154 cooperate to form an electric field. This electric field is oriented generally orthogonal to the electric field form from the tripolar electrode arrangement of FIG. 20.

In other embodiments, additional electrodes from the second arrangement 157 on one of both leads 152, 154 can cooperate to form the electric field. For example, FIG. 21 also shows a therapy signal channel between a first electrode 157a and a second electrode 157b. The therapy channel is angled with respect to the leads 152, 154. Such an angle may facilitate applying the therapy signal along the length of a dorsal root DR as the root branches from the dorsal column DC.

In the above paragraphs, a number of therapy combinations have been described which include dorsal column low frequency stimulation and/or high frequency blocking, dorsal root high frequency blocking, and peripheral nerve high frequency blocking. Procedures to avoid patient discomfort in the onset and subsequent therapy phases also have been discussed. In other embodiments, therapy can be performed in accordance with other permutations and combinations of the aforementioned parameters, time variations, and therapeutic phases.

Figure 22:
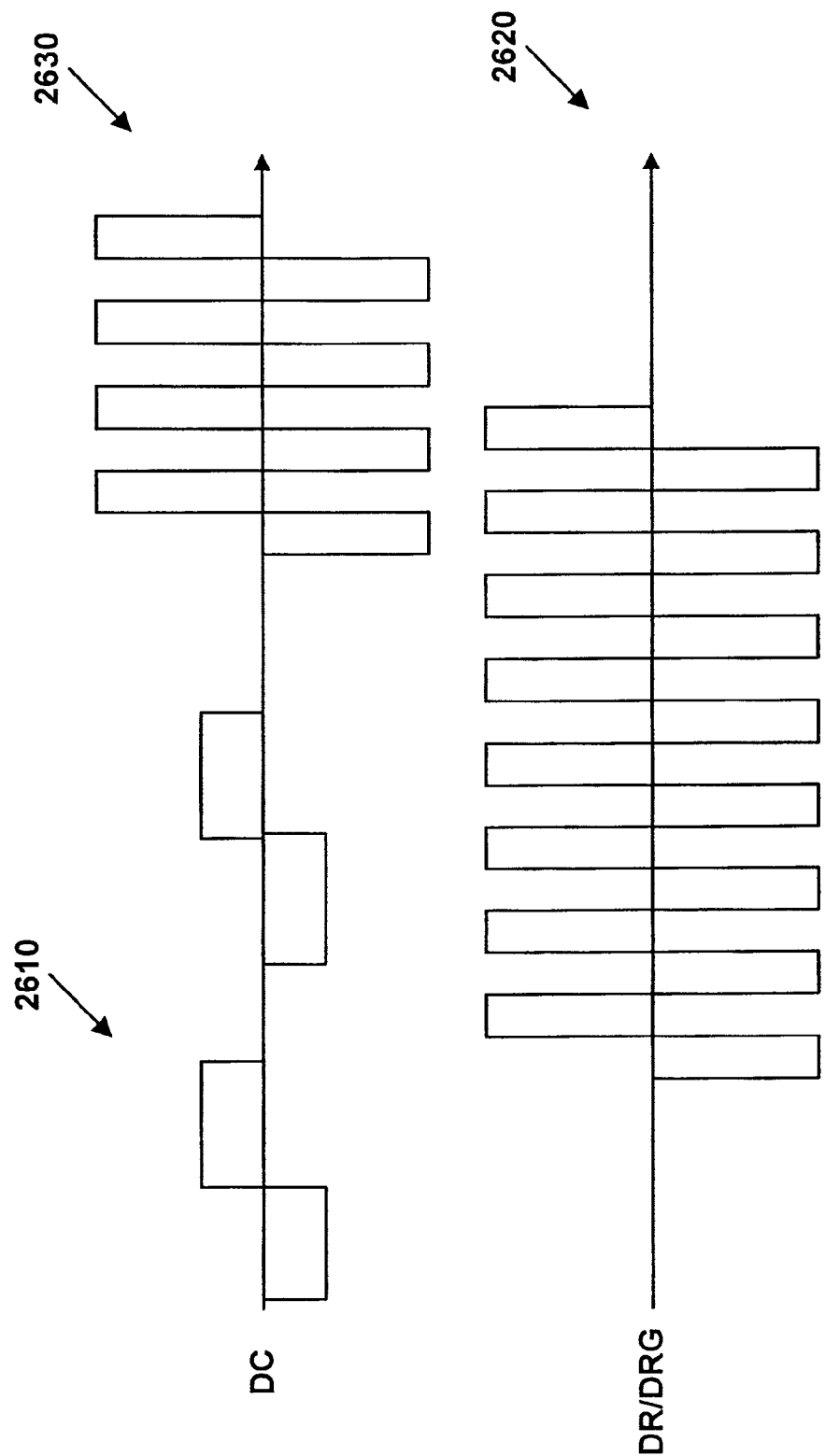
FIG. 22 illustrates a first treatment signal being applied to nerves of a dorsal column of a patient in accordance with an embodiment of the present disclosure.

To aid in understanding the above described treatment options, the following example applications are provided. FIG. 22 illustrates a first treatment signal 2610 being applied to nerves of a dorsal column DC of a patient. The first treatment signal 2610 is an LF signal configured to up-regulate the nerves of the dorsal column DC to induce a sensation of paresthesia, and can be provided by a first portion of the pulse generator 101 described above with reference to FIG. 1.

A second treatment signal 2620 is applied to a dorsal root DR of the patient subsequent to the initialization of the first treatment signal 2610. The second treatment signal 2620 is an HF signal configured to down-regulate the nerves of the dorsal root DR to establish a block on the nerves, and can be provided by a second portion of the pulse generator 101 described above with reference to FIG. 1. The paresthesia induced by the first treatment signal 2610 at least partially masks the onset response experienced by the patient when the second treatment signal 2620 is initiated.

As shown, a third treatment signal 2630 is applied to the dorsal column DC after the second treatment signal 2620 is initiated. In a particular embodiment, the third treatment signal 2630 is applied to the dorsal column DC after the second treatment signal 2620 establishes a block on the dorsal root DR. The third treatment signal 2630 is configured to establish a block on the dorsal column DC.

In another representative example, a practitioner can implant multiple electrodes at the patient's spinal region, with at least one of the electrodes positioned to provide spinal cord stimulation, and at least one of the electrodes positioned to apply signals to the dorsal root or the dorsal root ganglion. The practitioner can then apply an LF signal to the first electrode to induce paresthesia and address pain suffered by the patient. In at least some cases, the paresthesia may be sufficient to address the patient's pain symptoms, and accordingly, an HF signal need not be applied to the second electrode. In other instances, however, an initial LF signal applied to the first electrode may not adequately address the patient's pain. In such instances, the amplitude of the signal supplied to the first electrode may be increased to produce paresthesia. The increase may be required because the position of the first electrode is not optimal, and/or because of patient-specific physiological effects. In any of these embodiments, increasing the amplitude of the signal applied to the first electrode may, at the same time it causes paresthesia, separately cause patient discomfort. Accordingly, the practitioner can apply HF signals to the second electrode to block the patient discomfort, without the need for repositioning the first electrode. This arrangement can accordingly reduce the invasiveness of the implantation procedure.

In another example, the patient may suffer from lower back pain. The lower back pain may be transmitted along afferent nerve fibers that enter the spinal column channel at the L5 vertebrae, which is below the end of the spinal cord. Accordingly, the practitioner may apply LF spinal cord stimulation at a higher spinal elevation, for example, at the T10 vertebrae. In at least some instances, the paresthesia resulting from such LF signals may reduce pain somewhat, but not completely. Accordingly, the practitioner may additionally apply HF signals at the L5 location to block lower back pain sensations. In this instance, the HF signal is applied at a different spinal elevation than the low frequency signal.

In still another example, the patient may suffer from pain transmitted along several neural pathways that enter the spinal column at L1 (e.g., at the conus). The practitioner may apply HF signals at the conus, in combination with LF signals at a higher spinal elevation (e.g., T8, T9 or T10). This is unlike several existing stimulation techniques, which deliberately avoid the conus as an implantation/stimulation site.

From the foregoing, it will be appreciated that specific embodiments of the disclosure have been described herein for purposes of illustration, but that various modifications may be made without deviating from the disclosure. For example, the LF signals may be provided on a generally continuous basis in some embodiments, and may be turned off and on automatically in other embodiments, or in response to a patient request in still further embodiments. In some embodiments, directions and/or instructions were described in the context of a pulse generator, and in other embodiments, such directions and/or instructions may be handled by other controller components. Certain aspects of the disclosure described in the context of particular embodiments may be combined or eliminated in other embodiments. For example, while HF and LF signals were discussed in the context of lower back pain and applied to different spinal elevations, in other embodiments, such signals may be applied at different spinal elevations to address other patient pain symptoms. Further, while advantages associated with certain embodiments have been described in the context of those embodiments, other embodiments may also exhibit such advantages. Not all embodiments need necessarily exhibit such advantages to fall within the scope of the disclosure. Accordingly, the disclosure can include other embodiments not shown or described above.

We claim:

1. A method for alleviating patient pain or discomfort, without relying on paresthesia or tingling to mask the patient's sensation of the pain, comprising:
    implanting a percutaneous lead in the patient's epidural space, wherein the percutaneous lead includes at least one electrode, and wherein implanting the percutaneous lead includes positioning the at least one electrode proximate to a target location in the patient's spinal cord region and outside the sacral region;
    implanting a signal generator in the patient;
    electrically coupling the percutaneous lead to the signal generator; and
    programming the signal generator to generate and deliver an electrical therapy signal to the spinal cord region, via the at least one electrode, wherein at least a portion of the electrical therapy signal is at a frequency in a frequency range of from about 2,500 Hz to about 100,000 Hz.

2. The method of claim 1 wherein the target location includes the patient's dorsal column.

3. The method of claim 1 wherein the at least one electrode is located toward a distal end of the percutaneous lead.

4. The method of claim 1, wherein at least a portion of the electrical therapy signal is at a frequency in a frequency range of from about 2,500 Hz to about 20,000 Hz.

5. The method of claim 1, wherein at least a portion of the electrical therapy signal is at a frequency in a frequency range of from about 3,000 Hz to about 10,000 Hz.

6. The method of claim 1, further comprising:
applying a stimulation signal to the patient's spinal cord region, wherein the stimulation signal is at a frequency in a frequency range of from about 40 Hz to about 500 Hz.

7. The method of claim 1, wherein the electrical therapy signal is applied continuously.

8. The method of claim 1, wherein the electrical therapy signal is applied discontinuously so as to include periods when the electrical therapy signal is applied, and periods when the electrical therapy signal is terminated.

9. The method of claim 8, wherein the periods when the electrical therapy signal is applied range from a few seconds to a few hours.

10. The method of claim 1, wherein the electrical therapy signal is applied discontinuously so as to include periods when the electrical therapy signal is applied, and periods when the electrical therapy signal is terminated according to a duty cycle.

11. A method for alleviating patient pain or discomfort, without relying on paresthesia or tingling to mask the patient's sensation of the pain, comprising:

implanting a percutaneous lead in the patient's epidural space, wherein the percutaneous lead includes at least one electrode, and wherein implanting the percutaneous lead includes positioning the at least one electrode proximate to a target location in the patient's spinal cord region and outside the scaral region;

implanting a signal generator in the patient;

electrically coupling the percutaneous lead to the signal generator; and programming the signal generator to generate and deliver an electrical therapy signal to the spinal cord region, via the at least one electrode, wherein at least a portion of the electrical therapy signal is at a frequency in a frequency range of from about 2,500 Hz to about 100,000 Hz and a current amplitude between about 2 mA and about 20 mA.

12. The method of claim 11, further comprising:
programming the signal generator to generate and deliver the electrical therapy signal at a duty cycle of less than 50%.

* * * * *

UNITED STATES PATENT AND TRADEMARK OFFICE
CERTIFICATE OF CORRECTION

| | | |
|---|---|---|
| PATENT NO. | : 8,768,472 B2 | Page 1 of 1 |
| APPLICATION NO. | : 13/705021 | |
| DATED | : July 1, 2014 | |
| INVENTOR(S) | : Zi-Ping Fang et al. | |

It is certified that error appears in the above-identified patent and that said Letters Patent is hereby corrected as shown below:

ON THE TITLE PAGE

On page 3, in column 2, under "Other Publications", line 21, delete "Sterotactic" and insert -- Stereotactic --, therefor.

On page 4, in column 1, under "Other Publications", line 8, delete "Techinical" and insert -- Technical --, therefor.

On page 4, in column 1, under "Other Publications", line 14, delete "Spianl" and insert -- Spinal --, therefor.

On page 4, in column 1, under "Other Publications", line 42, delete "Offical" and insert -- Official --, therefor.

On page 4, in column 2, under "Other Publications", line 35, delete "Bandra et al.," and insert -- Bahdra et al., --, therefor.

IN THE SPECIFICATION

In column 3, line 7, delete "parethesia" and insert -- paresthesia --, therefor.

IN THE CLAIMS

In column 22, line 6, in claim 11, delete "scaral" and insert -- Sacral --, therefor.

Signed and Sealed this
Twenty-sixth Day of January, 2016

Michelle K. Lee
*Director of the United States Patent and Trademark Office*